United States Patent [19]

Sato et al.

[11] 4,426,382

[45] Jan. 17, 1984

[54] 4-AMINO-6,7-DIMETHOXY-2-PIPERAZINYLQUINAZOLINE DERIVATIVES, THEIR PREPARATION AND USE

[75] Inventors: Yasunobu Sato; Hiroshi Fukumi; Hiroyuki Koike; Hiroshi Nishino, all of Hiromachi, Japan

[73] Assignee: Sankyo Company Limited, Tokyo, Japan

[21] Appl. No.: 233,679

[22] Filed: Feb. 11, 1981

[30] Foreign Application Priority Data

Feb. 13, 1980 [JP] Japan ................... 55-16775
Apr. 21, 1980 [JP] Japan ................... 55-52754
Jul. 14, 1980 [JP] Japan ................... 55-96106
Jul. 14, 1980 [JP] Japan ................... 55-96107

[51] Int. Cl.$^3$ ................ A61K 31/505; C07D 403/04
[52] U.S. Cl. ......................... 424/251; 542/431; 544/291; 260/243.3
[58] Field of Search ................ 424/251; 544/291; 542/431; 260/243.3

[56] References Cited

U.S. PATENT DOCUMENTS 3,635,979  1/1972  Hess .................... 544/291
3,935,213  1/1976  Hess .................... 544/291
4,287,341  9/1981  Hess et al. ............. 544/291

FOREIGN PATENT DOCUMENTS

WO79/00166  4/1979  PCT Int'l Appl. ............. 544/291

OTHER PUBLICATIONS

"Life Science", vol. 27, 1980, pp. 1525-1540.
*Physician's Desk Reference*, 1981, pp. 1412-1413.

*Primary Examiner*—Donald G. Daus
*Assistant Examiner*—James H. Turnipseed
*Attorney, Agent, or Firm*—Frishauf, Holtz, Goodman & Woodward

[57] ABSTRACT

Novel piperazinylquinazoline and homopiperazinylquinazoline compounds which have useful antihypertensive activity and their use including pharmaceutical compositions containing said derivatives as the active antihypertensive component thereof. Said compounds have the following formula.

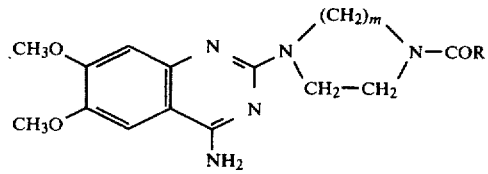

wherein m is 2 or 3 and R is as defined in the specification.

50 Claims, No Drawings

4-AMINO-6,7-DIMETHOXY-2-PIPERAZINYL-QUINAZOLINE DERIVATIVES, THEIR PREPARATION AND USE

BACKGROUND OF THE INVENTION

The present invention relates to a series of new piperazinylquinazoline and homopiperazinylquinazoline derivatives which have valuable antihypertensive activity, to methods for the preparation of such compounds and to their use.

A variety of quinazoline derivatives, including some piperazinyl- and homopiperazinyl-quinazoline derivatives, are known and many of these are known to have hypotensive (or antihypertensive) activity. For example, U.S. Pat. No. 3,511,836 discloses as having valuable hypotensive properties a very considerable number of quinazoline derivatives, including some which may be represented by the formula:

in which:

$R^a$ and $R^b$ each represent hydrogen atoms or $C_1$–$C_3$ alkoxy groups, at least one of them being an alkoxy group, $R^c$ and $R^d$ each represent hydrogen atoms, alkyl groups, alkenyl groups, hydroxyalkyl groups, phenyl groups, benzyl groups, phenethyl groups, furfuryl groups or cycloalkyl groups, and Z represents, amongst many other alternatives, an alkanoyl group, a benzoyl group or a 3,4,5-trimethoxybenzoyl group.

U.S. Pat. No. 4,060,615 also discloses a variety of piperazinylquinazoline derivatives, which may be represented by the general formula:

in which:

$R^e$ represents an amino or hydrazino group; and $R^f$ represents a cycloalkyl, methylcycloalkyl or cycloalkenyl group.

U.S. Pat. No. 3,920,636 discloses a series of 4-amino-2-(4-substituted homopiperazinyl-6,7-dimethoxyquinazoline derivatives and suggests that they may be used as hypotensive agents.

In practice, however, only one of these known quinazoline derivatives has actually been used. This compound, which is one of the compounds disclosed in U.S. Pat. No. 3,511,836 is known by the name prazosin and has the formula:

Although prazosin has very useful antihypertensive activity, its maximum hypotensive effect tends to be achieved very quickly and the effect tends also to diappear quickly: the very rapid hypotensive effect of prazosin can cause problems and its rapid disappearance means that the compound must be administered frequently. There is, therefore, a need for compounds which develop their antihypertensive activity more slowly and where the antihypertensive effect is prolonged. Moreover, of course, there is a need for compounds having better antihypertensive activity than prazosin.

BRIEF SUMMARY OF INVENTION

We have now found a series of new quinazoline derivatives which have antihypertensive activity and many of which are, in one or another of the ways suggested above, better than the known drug prazosin.

The compounds of the invention are those compounds of formula (I):

in which:

m is 2 or 3; and

R represents a $C_2$–$C_9$ alkenyl group, a $C_2$–$C_9$ alkynyl group, a $C_4$–$C_9$ alkadienyl group, a group of formula:

(where:

$R^1$ represents a hydrogen atom or an alkyl group and the two groups $R^1$ may be the same or different;

$R^2$ represents a phenyl group optionally having one or more alkyl, alkoxy or halogen substituents;

$R^3$ represents an alkyl group, an alkoxy group, a hydroxy group, a halogen atom or a group of formula —$[O(CR^1{}_2)_nR^2]$ and, where there is more than one group $R^3$, they may be the same or different;

n is 0 or an integer from 1 to 3; and

P is 0, 1 or 2), a group of formula:

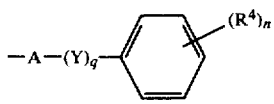

(where:
A represents a bivalent saturated aliphatic hydrocarbon a group;
Y represents an oxygen atom or a sulphur atom;
q is 0 or 1;
$R^4$ represents an alkyl group, a hydroxy group, an alkoxy group, a halogen atom or an amino group optionally having one or two alkyl and/or acyl substituents; and
n is as defined above),
a group of formula:

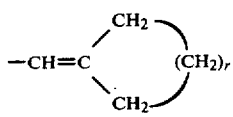

(where:
r is an integer from 1 to 5),
or a group of formula:

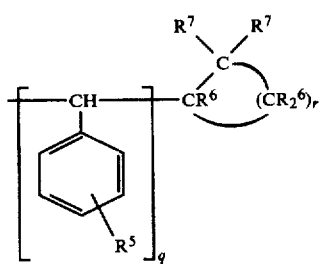

(where:
$R^5$ represents a hydrogen atom, an alkyl group, an alkoxy group or a halogen atom;
one of the symbols $R^6$ represents a hydrogen atom, a phenyl group or a substituted phenyl group having one or more alkyl, alkoxy or halogen atom substituents and the other symbols $R^6$ all represent hydrogen atoms;
$R^7$ represents a hydrogen atom, an alkyl group or a halogen atom; and
q and r are as defined above;
provided that, when q is 0, one of the symbols $R^6$ represents a substituted or unsubstituted phenyl group).

These compounds are capable of forming acid addition salts and hence the invention also provides pharmaceutically acceptable acid addition salts of the compounds of formula (I).

The compounds of formula (I) may be prepared by:
(a) condensing a 2-haloquinazoline derivative of formula (II):

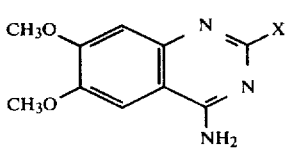

(in which X represents a halogen atom) with a piperazine or homopiperazine derivative of formula (III):

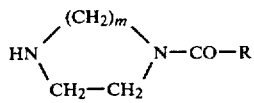

(in which m and R are as defined above), by dehydrohalogenation; or (b) condensing a quinazoline derivative of formula (IV):

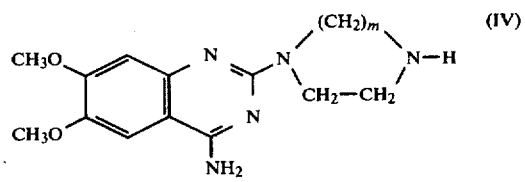

(in which m is as defined above) with a carboxylic acid of formula (V):

$$HOOC-R \qquad (V)$$

(in which R is as defined above) or with a reactive derivative of said carboxylic acid.

The invention still further provides pharmaceutical compositions comprising a compound of formula (I) or an acid addition salt thereof in admixture with a pharmaceutically acceptable carrier or diluent.

DETAILED DESCRIPTION OF INVENTION

Amongst the compounds of the invention, one preferred class is those compounds of formula (Ia):

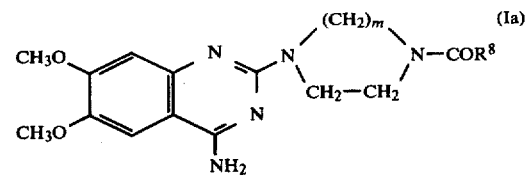

in which
m is as defined above; and
$R^8$ represents a $C_2$–$C_9$ alkenyl group, a $C_2$–$C_9$ alkynyl group or a $C_4$–$C_9$ alkadienyl group.

Where $R^8$ represents a $C_2$–$C_9$ alkenyl group, this group may be straight or branched chain. Examples of such groups include the vinyl, 1-methylvinyl, 1-propenyl, allyl, 1-ethylvinyl, 1-butenyl, 2-butenyl, 3-butenyl, 2-methyl-1-propenyl, 1-methyl-1-propenyl, 2-methylallyl, 1-propylvinyl, 1-pentenyl, 2-pentenyl, 3-pentenyl, 4-pentenyl, 1-methyl-1-butenyl, 2-methyl-1-butenyl, 3-methyl-2-butenyl, 1-methyl-3-butenyl, 2-methyl-2-butenyl, 1,1-dimethyl-2-propenyl, 1-methyl-1-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1,3-dimethyl-5-hexenyl, 1-nonenyl, 2-nonenyl, 3-nonenyl, 4-nonenyl, 5-nonenyl, 6-nonenyl, 7-nonenyl and 8-nonenyl groups.

Where $R^8$ represents a $C_2$-$C_9$ alkynyl group, this group may be straight or branched chain. Examples of such groups include the ethynyl, 1-propynyl, 1-methyl-3-butynyl, 1-hexynyl and 1-octynyl groups.

Where $R^8$ represents a $C_4$-$C_9$ alkadienyl group, this is preferably a 1,3-butadienyl, 1,3-pentadienyl, 2,4-petadienyl, 1,4-dimethyl-1,3-pentadienyl or 1,3-nonadienyl group.

Of the compounds of formula (Ia), preferred compounds are those where $R^8$ represents a $C_3$ or $C_4$ alkenyl group, more preferably a 1-propenyl, 1-butenyl or 3-butenyl group.

A further preferred class of compounds is represented by those compounds of formula (Ib):

A further preferred class of compounds of the invention is represented by those compounds of formula (Ic):

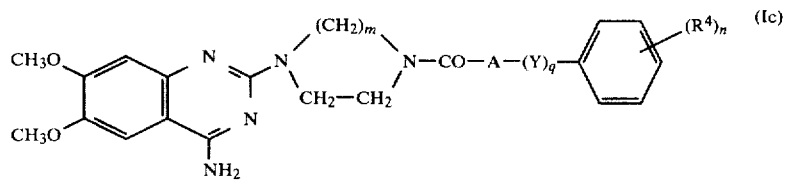

in which:

m, n, q, A, Y and $R^4$ are as defined above.

Where $R^4$ represents an alkyl group, this is preferably a lower alkyl group and may be straight or branched chain. Preferred alkyl groups have from 1 to 3 carbon atoms; such groups are the methyl, ethyl, propyl and isopropyl groups. Where $R^4$ represents an alkoxy group, this is preferably a lower alkoxy group and may be a straight or branched chain group. Preferred alkoxy groups have from 1 to 3 carbon atoms; such groups are the methoxy, ethoxy, propoxy and isopropoxy groups. Where $R^4$ represents a halogen atom, this is preferably a fluorine, chlorine or bromine atom. Where $R^4$ represents an amino group, this may have 1 or 2 substituents selected from alkyl and acyl groups. The alkyl substitu-

[structure Ib with $[O(CH_2)_nR^2]_x$]

in which:

m, n and $R^2$ are as defined above; and x is an integer from 1 to 3.

In the compounds of formula (Ib), $R^2$ may represent an unsubstituted phenyl group or it may represent a phenyl group having one or more substituents selected from lower alkyl groups, lower alkoxy groups and halogen atoms. Preferred alkyl substituents, which may be straight or branched chain, have from 1 to 3 carbon atoms; such alkyl groups are the methyl, ethyl, propyl and isopropyl groups. Preferred alkoxy substituents, which may be straight or branched chain, have from 1 to 3 carbon atoms; such groups are the methoxy, ethoxy, propoxy and isopropoxy groups. Preferred halogen atoms are the fluorine, chlorine or bromine atoms. Where the phenyl group represented by $R^2$ is substituted, there are preferably 1 or 2 substituents, although, if desired, there may be more, and these are preferably in the ortho and/para positions.

In the compounds of formula (Ib), n may be 0 or an integer from 1 to 3 and is preferably 1. The integer represented by x may be from 1 to 3 and is also preferably 1. The group $[O(CH_2)_nR^2]$ may be in any of the 2, 3, 4, 5 or 6 positions of the benzene ring which it substitutes, but it is preferably in the 4-position.

ents, which may be straight or branched chain, preferably have from 1 to 3 carbon atoms and are thus preferably the methyl, ethyl, propyl or isopropyl groups. The acyl substituents also preferably have from 1 to 3 carbon atoms and are thus the formyl, acetyl or propionyl groups.

A represents a bivalent saturated aliphatic hydrocarbon group, which may be straight or branched chain and which preferably has from 1 to 6 carbon atoms. Examples of such groups represented by A include the methylene, ethylene, trimethylene, tetramethylene, ethylidene, propylidene, butylidene, 1-methylethylene, 2-methylethylene, 1,2-dimethylethylene, 1-ethylethylene, 2-ethylethylene, 1,2-diethylethylene, 1-propylethylene, 2-propylethylene, 1-methyl-2-ethylethylene, 1-methyltrimethylene, 1-ethyltrimethylene, 1-methyltetramethylene and 1-ethyltetramethylene groups. Particularly preferred are those compounds where A represents a methylene or an ethylene group.

Where the compound of formula (Ic) contains an oxygen or sulphur atom represented by Y, this is preferably an oxygen atom. Preferably the phenyl group shown in formula (Ic) is unsubstituted, i.e. n is 0.

A further preferred class of compounds of the invention is represented by formula (Id):

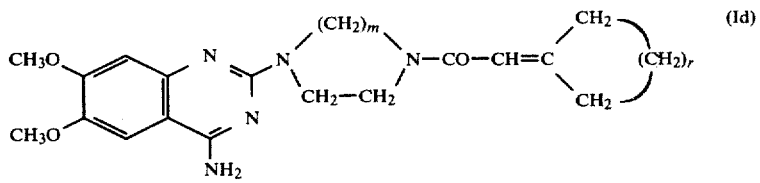

in which:

m is as defined above.

In the compounds of formula (Id), r represents an integer from 1 to 5, preferably from 2 to 4 and more preferably 2 or 3.

A further preferred class of compunds is represented by formula (Ie):

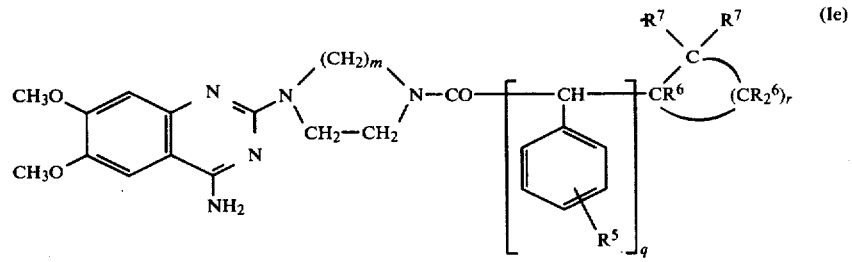

in which $R^5$, $R^6$, $R^7$, m, q, and r are as defined above.

Where $R^5$ represents an alkyl group, it may be a straight or branched chain alkyl group and preferably has from 1 to 3 carbon atoms, i.e. a methyl, ethyl, propyl or isopropyl group. Where $R^5$ represents an alkoxy group, it may be straight or branched chain group and preferably has from 1 to 3 carbon atoms, i.e. a methoxy, ethoxy, propoxy or isopropoxy group. Where $R^5$ represents a halogen atom, it is preferably a fluorine, chlorine or bromine atom.

Where $R^6$ represents a phenyl group, this may be unsubstituted or may have one or more substituents selected from alkyl groups, alkoxy groups and halogen atoms, preferably straight or branched chain $C_1$-$C_3$ alkyl groups (methyl, ethyl, propyl or isopropyl), straight or branched chain $C_1$-$C_3$ alkoxy groups (methoxy, ethoxy, propoxy or isopropoxy) or halogen atoms such as fluorine, chlorine or bromine atoms.

The two groups $R^7$ in the compound of formula (Ie) are normally and preferably the same. Where they represent alkyl groups, these are preferably lower alkyl groups, particularly methyl or ethyl groups, and where they represent halogen atoms, these are preferably fluorine, chlorine or bromine atoms.

Particularly preferred compounds are those in which r is 1, $R^6$ represents an unsubstituted phenyl group and the groups $R^7$ both represent hydrogen atoms.

A further preferred class of compounds of the invention is defined by those compounds of formula (If):

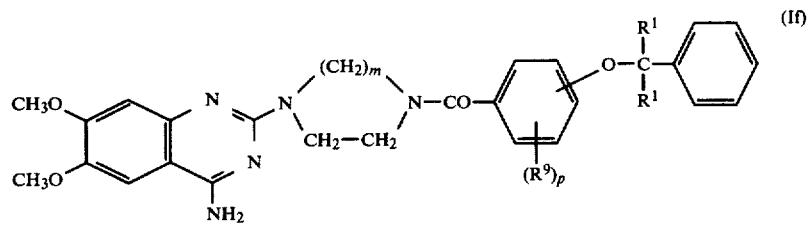

(in which m, p and $R^1$ are as defined above and $R^9$ represents an alkyl group, an alkoxy group, a hydroxy group or a halogen atom), of which the more preferred compounds are those in which the benzyloxy group is in the para position of the benzoyl group, that is to say compounds of formula (Ig):

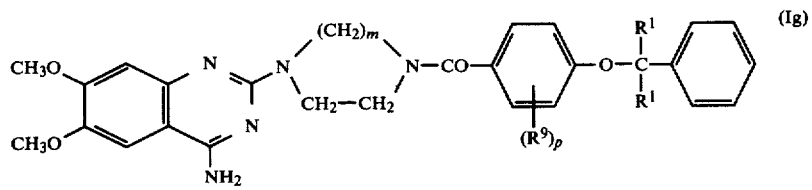

In the compounds of formulae (If) and (Ig), the two groups $R^1$ may be the same or different. Where $R^1$ represents an alkyl group, this may be a straight or branched chain alkyl group and preferably has from 1 to 3 carbon atoms, i.e. methyl, ethyl, propyl or isopropyl.

Where $R^9$ represents an alkyl group, this may be a straight or branched chain alkyl group and preferably has from 1 to 3 carbon atoms, i.e. methyl, ethyl, propyl or isopropyl. Where $R^9$ represents an alkoxy group, this may be a straight or branched chain alkoxy group and preferably has from 1 to 3 carbon atoms, i.e. methoxy, ethoxy, propoxy or isopropoxy. Where $R^9$ represents a halogen atom, it is preferably a fluorine, chlorine or bromine atom.

We particularly prefer those compounds where one of the symbols $R^1$ represents a hydrogen atom and the other represents a hydrogen atom or an alkyl (more preferably methyl) group and those compounds where p is 0 or 1.

In all of the compounds of formula (I), including the compounds of the formula (Ia)–(Ig), we particularly prefer those compounds where m is 2, that is to say the piperazinylquinazoline derivatives.

Many of the compounds of formula (I) can exist in the form of stereoisomers (including optical isomers and geometric isomers) due to the presence of asymmetric carbon atoms, carbon-carbon double bonds or non-planar ring systems. Although all of these isomers are represented above by a single formula, the present invention encompasses both the individual isomers as well as mixtures of two or more isomers.

The following are examples of compounds falling within the scope of the present invention. Where appropriate, the compounds are hereinafter referred to by the numbers appended to them in the following list:

1. 4-Amino-2-(4-crotonoyl-1-piperazinyl)-6,7-dimethoxyquinazoline.
2. 4-Amino-6,7-dimethoxy-2-[4-(2-methylacryloyl)-1-piperazinyl]quinazoline.
3. 4-Amino-2-[4-(2,3-dimethylacryloyl)-1-piperazinyl]-6,7-dimethoxyquinazoline.
4. 4-Amino-2-[4-(3,3-dimethylacryloyl)-1-piperazinyl]-6,7-dimethoxyquinazoline.
5. 4-Amino-6,7-dimethoxy-2-[4-(2-pentenoyl)-1-piperazinyl]quinazoline.
6. 4-Amino-6,7-dimethoxy-2-[4-(4-pentenoyl)-1-piperazinyl]quinazoline.
7. 4-Amino-2-[4-(3-hexenoyl)-1-piperazinyl]-6,7-dimethoxyquinazoline.
8. 4-Amino-2-[4-(2-hexenoyl)-1-piperazinyl]-6,7-dimethoxyquinazoline.
9. 4-Amino-2-(4-crotonoyl-1-homopiperazinyl)-6,7-dimethoxyquinazoline.
10. 4-Amino-2-[4-(2,4-hexadienoyl)-1-piperazinyl]-6,7-dimethoxyquinazoline.
11. 4-Amino-6,7-dimethoxy-2-(4-tetroyl-1-piperazinyl)quinazoline.
12. 4-Amino-2-[4-(2-benzyloxybenzoyl)-1-piperazinyl]-6,7-dimethoxyquinazoline.
13. 4-Amino-2-[4-(3-benzyloxybenzoyl)-1-piperazinyl]-6,7-dimethoxyquinazoline.
14. 4-Amino-2-[4-(4-benzyloxybenzoyl)-1-piperazinyl]-6,7-dimethoxyquinazoline.
15. 4-Amino-2-[4-(4-benzyloxybenzoyl)-1-homopiperazinyl]-6,7-dimethoxyquinazoline.
16. 4-Amino-6,7-dimethoxy-2-[4-(2-phenoxybenzoyl)-1-piperazinyl]quinazoline.
17. 4-Amino-6,7-dimethoxy-2-[4-(3-phenoxybenzoyl)-1-piperazinyl]quinazoline.
18. 4-Amino-6,7-dimethoxy-2-[4-(4-phenoxybenzoyl)-1-piperazinyl]quinazoline.
19. 4-Amino-6,7-dimethoxy-2-[4-(2-phenethoxybenzoyl)-1-piperazinyl]quinazoline.
20. 4-Amino-6,7-dimethoxy-2-[4-(3-phenethoxybenzoyl)-1-piperazinyl]quinazoline.
21. 4-Amino-6,7-dimethoxy-2-[4-(4-phenethoxybenzoyl)-1-piperazinyl]quinazoline.
22. 4-Amino-2-[4-(4-4'-chlorobenzyloxybenzoyl)-1-piperazinyl]-6,7-dimethoxyquinazoline.
23. 4-Amino-6,7-dimethoxy-2-[4-(4-4'-methylbenzyloxybenzoyl)-1-piperazinyl]quinazoline.
24. 4-Amino-2-[4-(4-2',4'-dichlorobenzyloxybenzoyl)-1-piperazinyl]-6,7-dimethoxyquinazoline.
25. 4-Amino-6,7-dimethoxy-2-[4-(2-phenoxypropionyl)-1-piperazinyl]quinazoline.
26. 4-Amino-6,7-dimethoxy-2-[4-(3-phenoxypropionyl)-1-piperazinyl]quinazoline.
27. 4-Amino-6,7-dimethoxy-2-(4-phenoxacetyl-1-piperazinyl)quinazoline.
28. 4-Amino-6,7-dimethoxy-2-(4-phenylacetyl-1-piperazinyl)quinazoline.
29. 4-Amino-6,7-dimethoxy-2-[4-(3-phenylpropionyl)-1-piperazinyl]quinazoline.
30. 4-Amino-6,7-dimethoxy-2-(4-phenylthioacetyl-1-piperazinyl)quinazoline.
31. 4-Amino-2-(4-cyclohexylideneacetyl-1-piperazinyl)-6,7-dimethoxyquinazoline.
32. 4-Amino-2-(4-cyclopentylideneacetyl-1-piperazinyl)-6,7-dimethoxyquinazoline.
33. 4-Amino-6,7-dimethoxy-2-[4-(1-phenylcyclopropylcarbonyl)-1-piperazinyl]quinazoline.
34. 4-Amino-6,7-dimethoxy-2-[4-(trans-2-phenylcyclopropylcarbonyl)-1-piperazinyl]quinazoline.
35. 4-Amino-6,7-dimethoxy-2-[4-(cis-2-phenylcyclopropylcarbonyl)-1-piperazinyl]quinazoline.
36. 4-Amino-6,7-dimethoxy-2-[4-(trans-2-o-tolylcyclopropylcarbonyl)-1-piperazinyl]quinazoline.
37. 4-Amino-6,7-dimethoxy-2-[4-(cis-2-o-tolylcyclopropylcarbonyl)-1-piperazinyl]quinazoline.
38. 4-Amino-6,7-dimethoxy-2-[4-(trans-2-m-tolylcyclopropylcarbonyl)-1-piperazinyl]quinazoline.
39. 4-Amino-6,7-dimethoxy-2-[4-(trans-2-p-tolylcyclopropylcarbonyl)-1-piperazinyl]quinazoline.
40. 4-Amino-6,7-dimethoxy-2-[4-(trans-2-o-methoxyphenylcyclopropylcarbonyl)-1-piperazinyl]quinazoline.
41. 4-Amino-6,7-dimethoxy-2-[4-(trans-2-m-methoxyphenylcyclopropylcarbonyl)-1-piperazinyl]quinazoline.
42. 4-Amino-6,7-dimethoxy-2-[4-(cis-2-m-methoxyphenylcyclopropylcarbonyl)-1-piperazinyl]quinazoline.
43. 4-Amino-6,7-dimethoxy-2-[4-(trans-2-p-methoxyphenylcyclopropylcarbonyl)-1-piperazinyl]quinazoline.
44. 4-Amino-2-[4-(trans-2p-fluorophenylcyclopropylcarbonyl)-1piperazinyl]-6,7-dimethoxyquinazoline.
45. 4-Amino-2-[4-(trans-2-o-chlorophenylcyclopropylcarbonyl)-1-piperazinyl]-6,7-dimethoxyquinazoline.
46. 4-Amino-2-[4-(trans-2-m-chlorophenylcyclopropylcarbonyl)-1-piperazinyl]-6,7-dimethoxyquinazoline.
47. 4-Amino-2-[4-(trans-2-p-chlorophenylcyclopropylcarbonyl)-1-piperazinyl]-6,7-dimethoxquinazoline.
48. 4-Amino-2-[4-(cis-2-p-chlorophenylcyclopropylcarbonyl)-1-piperazinyl]-6,7-dimethoxyquinazoline.
49. 4-Amino-2-[4-(trans-2-p-bromophenylcyclopropylcarbonyl)-1-piperazinyl]-6,7-dimethoxyquinazoline.
50. 4-Amino-2-[4-(trans-3,3-dimethyl-2-phenylcyclopropylcarbonyl)-1-piperazinyl]-6,7-dimethoxyquinazoline.
51. 4-Amino-2-[4-(trans-3,3-dimethyl-2-p-tolylcyclopropylcarbonyl)-1-piperazinyl]-6,7-dimethoxyquinazoline.

52. 4-Amino-6,7-dimethoxy-2-[4-(trans-2-p-methoxyphenyl-3,3-dimethylcyclopropylcarbonyl)-1-piperazinyl]quinazoline.
53. 4-Amino-2-[4-(trans-2-p-chlorophenyl-3,3-dimethylcyclopropylcarbonyl)-1-piperazinyl]-6,7-dimethoxyquinazoline.
54. 4-Amino-2-[4-(trans-3,3-dichloro-2-phenylcyclopropylcarbonyl)-1-piperazinyl]-6,7-dimethoxyquinazoline.
55. 4-Amino-2-[4-(cis-3,3-dichloro-2-phenylcyclopropylcarbonyl)-1-piperazinyl]-6,7-dimethoxyquinazoline.
56. 4-Amino-2-[4-(trans-3,3-dibromo-2-phenylcyclopropylcarbonyl)-1-piperazinyl]-6,7-dimethoxyquinazoline.
57. 4-Amino-6,7-dimethoxy-2-[4-(1-phenylcyclobutylcarbonyl)-1-piperazinyl]quinazoline.
58. 4-Amino-6,7-dimethoxy-2-[4-(trans-2-phenylcyclobutylcarbonyl)-1-piperazinyl]quinazoline.
59. 4-Amino-6,7-dimethoxy-2-[4-(trans-3-phenylcyclobutylcarbonyl)-1-piperazinyl]quinazoline.
60. 4-Amino-6,7-dimethoxy-2-[4-(1-phenylcyclopentylcarbonyl)-1-piperazinyl]quinazoline.
61. 4-Amino-6,7-dimethoxy-2-[4-(trans-2-phenylcyclopentylcarbonyl)-1-piperazinyl]quinazoline.
62. 4-Amino-6,7-dimethoxy-2-[4-(trans-3-phenylcyclopentylcarbonyl)-1-piperazinyl]quinazoline.
63. 4-Amino-6,7-dimethoxy-2-[4-(1-phenylcyclohexylcarbonyl)-1-piperazinyl]quinazoline.
64. 4-Amino-6,7-dimethoxy-2-[4-(trans-2-phenylcyclohexylcarbonyl)-1-piperazinyl]quinazoline.
65. 4-Amino-6,7-dimethoxy-2-[4-(trans-3-phenylcyclohexylcarbonyl)-1-piperazinyl]quinazoline.
66. 4-Amino-6,7-dimethoxy-2-[4-(trans-4-phenylcyclohexylcarbonyl)-1-piperazinyl]quinazoline.
67. 4-Amino-6,7-dimethoxy-2-[4-(1-phenylcycloheptylcarbonyl)-1-piperazinyl]quinazoline.
68. 4-Amino-2-[4-(2-cyclopropyl-2-phenylacetyl)-1-piperazinyl]-6,7-dimethoxyquinazoline.
69. 4-Amino-2-[4-(2-cyclopropyl-2-p-tolylacetyl)-1-piperazinyl]-6,7-dimethoxyquinazoline.
70. 4-Amino-2-[4-(2-cyclopropyl-2-p-methoxyphenylacetyl)-1-piperazinyl]-6,7-dimethoxyquinazoline.
71. 4-Amino-2-[4-(2-o-chlorophenyl-2-cyclopropylacetyl)-1-piperazinyl]-6,7-dimethoxyquinazoline.
72. 4-Amino-2-[4-(2-m-chlorophenyl-2-cyclopropylacetyl)-1-piperazinyl]-6,7-dimethoxyquinazoline.
73. 4-Amino-2-[4-(2-p-chlorophenyl-2-cyclopropylacetyl)-1-piperazinyl]-6,7-dimethoxyquinazoline.
74. 4-Amino-2-[4-(2-cyclobutyl-2-phenylacetyl)-1-piperazinyl]-6,7-dimethoxyquinazoline.
75. 4-Amino-2-[4-(2-cyclobutyl-2-o-tolylacetyl)-1-piperazinyl]-6,7-dimethoxyquinazoline.
76. 4-Amino-2-[4-(2-cyclobutyl-2-o-methoxyphenylacetyl)-1-piperazinyl]-6,7-dimethoxyquinazoline.
77. 4-Amino-2-[4-(2-o-chlorophenyl-2-cyclobutylacetyl)-1-piperazinyl]-6,7-dimethoxyquinazoline.
78. 4-Amino-2-[4-(2-p-chlorophenyl-2-cyclobutylacetyl)-1-piperazinyl]-6,7-dimethoxyquinazoline.
79. 4-Amino-2-[4-(2-cyclopentyl-2-phenylacetyl)-1-piperazinyl]-6,7-dimethoxyquinazoline.
80. 4-Amino-2-[4-(2-cyclopentyl-2-p-tolylacetyl)-1-piperazinyl]-6,7-dimethoxyquinazoline.
81. 4-Amino-2-[4-(2-cyclopentyl-2-p-methoxyphenylacetyl)-1-piperazinyl]-6,7-dimethoxyquinazoline.
82. 4-Amino-2-[4-(2-p-chlorophenyl-2-cyclopentylacetyl)piperazinyl]-6,7-dimethoxyquinazoline.
83. 4-Amino-2-[4-(2-cyclohexyl-2-phenylacetyl)-1-piperazinyl]-6,7-dimethoxyquinazoline.
84. 4-Amino-2-[4-(2-cyclohexyl-2-p-tolylacetyl)-1-piperazinyl]-6,7-dimethoxyquinazoline.
85. 4-Amino-2-[4-(2-cyclohexyl-2-p-methoxyphenylacetyl)-1-piperazinyl]-6,7-dimethoxyquinazoline.
86. 4-Amino-2-[4-(2-p-chlorophenyl-2-cyclohexylacetyl)-1-piperazinyl]-6,7-dimethoxyquinazoline.
87. 4-Amino-2-[4-(2-cycloheptyl-2-phenylacetyl)-1-piperazinyl]-6,7-dimethoxyquinazoline.
88. 4-Amino-2-[4-(2-cycloheptyl-2-p-tolylacetyl)-1-piperazinyl]-6,7-dimethoxyquinazoline.
89. 4-Amino-2-[4-(2-cycloheptyl-2-p-methoxyphenylacetyl)-1-piperazinyl]-6,7-dimethoxyquinazoline.
90. 4-Amino-2-[4-(2-p-chlorophenyl-2-cycloheptylacetyl)-1-piperazinyl]-6,7-dimethoxyquinazoline.
91. 4-Amino-2-[4-(4-benzyloxy-2-methylbenzoyl)-1-piperazinyl]-6,7-dimethoxyquinazoline.
92. 4-Amino-2-[4-(4-benzyloxy-3-methylbenzoyl)-1-piperazinyl]-6,7-dimethoxyquinazoline.
93. 4-Amino-2-[4-(4-benzyloxy-2-methoxybenzoyl)-1-piperazinyl]-6,7-dimethoxyquinazoline.
94. 4-Amino-2-[4-(4-benzyloxy-3-methoxybenzoyl)-1-piperazinyl]-6,7-dimethoxyquinazoline.
95. 4-Amino-2-[4-(4-benzyloxy-3-ethoxybenzoyl)-1-piperazinyl]-6,7-dimethoxyquinazoline.
96. 4-Amino-2-[4-(4-benzyloxy-3-propoxybenzoyl)-1-piperazinyl]-6,7-dimethoxyquinazoline.
97. 4-Amino-2-[4-(4-benzyloxy-2-chlorobenzoyl)-1-piperazinyl]-6,7-dimethoxyquinazoline.
98. 4-Amino-2-[4-(4-benzyloxy-3-chlorobenzoyl)-1-piperazinyl]-6,7-dimethoxyquinazoline.
99. 4-Amino-2-[4-(4-benzyloxy-2-fluorobenzoyl)-1-piperazinyl]-6,7-dimethoxyquinazoline.
100. 4-Amino-2-[4-(4-benzyloxy-3-fluorobenzoyl)-1-piperazinyl]-6,7-dimethoxyquinazoline.
101. 4-Amino-2-[4-(4-benzyloxy-2-bromobenzoyl)-1-piperazinyl]-6,7-dimethoxyquinazoline.
102. 4-Amino-2-[4-(4-benzyloxy-3-bromobenzoyl)-1-piperazinyl]-6,7-dimethoxyquinazoline.
103. 4-Amino-6,7-dimethoxy-2-[4-(4-1'-phenylethoxybenzoyl)-1-piperazinyl]quinazoline.
104. 4-Amino-6,7-dimethoxy-2-[4-(4-1'-phenylpropoxybenzoyl)-1-piperazinyl]quinazoline.
105. 4-Amino-6,7-dimethoxy-2-[4-(4-1'-phenylbutoxybenzoyl)-1-piperazinyl]quinazoline.
106. 4-Amino-6,7-dimethoxy-2-[4-(4-α',α'-dimethylbenzyloxybenzoyl)-1-piperazinyl]quinazoline.
107. 4-Amino-6,7-dimethoxy-2-[4-(4-1'-methyl-1'-phenylpropoxybenzoyl)-1-piperazinyl]quinazoline.
108. 4-Amino-6,7-dimethoxy-2-[4-(3-methyl-4-1'-phenylethoxybenzoyl)-1-piperazinyl]quinazoline.
109. 4-Amino-6,7-dimethoxy-2-[4-(3-methoxy-4-1'-phenylethoxybenzoyl)-1-piperazinyl]quinazoline.
110. 4-Amino-2-[4-(3-chloro-4-1'-phenylethoxybenzoyl)-1-piperazinyl]-6,7-dimethoxyquinazoline.
111. 4-Amino-6,7-dimethoxy-2-[4-(3-methyl-4-α',α'-dimethylbenzyloxybenzoyl)-1-piperazinyl]quinazoline.

112. 4-Amino-6,7-dimethoxy-2-[4-(3-methoxy-4-α',α'-dimethylbenzyloxybenzoyl)-1-piperazinyl]quinazoline.
113. 4-Amino-2-[4-(3-chloro-4-α',α'-dimethylbenzyloxybenzoyl)-1-piperazinyl]-6,7-dimethoxyquinazoline.
114. 4-Amino-2-[4-(4-benzyloxy-3,5-dimethoxybenzoyl)-1-piperazinyl]-6,7-dimethoxyquinazoline.
115. 4-Amino-2-[4-(4-benzyloxy-2,3-dimethoxybenzoyl)-1-piperazinyl]-6,7-dimethoxyquinazoline.
116. 4-Amino-2-[4-(4-benzyloxy-3-methylbenzoyl)-1-homopiperazinyl]-6,7-dimethoxyquinazoline.
117. 4-Amino-2-[4-(4-benzyloxy-3-methoxybenzoyl)-1-homopiperazinyl]-6,7-dimethoxyquinazoline.
118. 4-Amino-2-[4-(4-benzyloxy-3-chlorobenzoyl)-1-homopiperazinyl]-6,7-dimethoxyquinazoline.
119. 4-Amino-2-[4-(4-1'-phenylethoxybenzoyl)-1-homopiperazinyl]-6,7-dimethoxyquinazoline.
120. 4-Amino-2-[4-(4-1'-phenylpropoxybenzoyl)-1-homopiperazinyl]-6,7-dimethoxyquinazoline.
121. 4-Amino-2-[4-(3-benzyloxy-2-chlorobenzoyl)-1-piperazinyl]-6,7-dimethoxyquinazoline.
122. 4-Amino-2-[4-(2-benzyloxy-3-bromobenzoyl)-1-piperazinyl]-6,7-dimethoxyquinazoline.

Of these compounds, preferred compounds are Compounds No. 1, 5, 6, 14, 25, 27, 28, 29, 30, 31, 32, 33, 34, 94, 98, 103, 104, 106 and 114, of which Compounds No. 14, 25, 27, 29, 34 and 103 are particularly preferred.

The compounds of the invention are bases and thus can form acid addition salts. There is no particular limitation on the nature of the acid used to form such salts provided that, as is well-known in the art, the acid does not substantially increase the toxicity of the free base. Suitable acids include mineral acids (such as hydrochloric acid, phosphoric acid, sulphuric acid or nitric acid) and organic acids (such as tartaric acid, citric acid, malic acid, lactic acid, ascorbic acid, fumaric acid and maleic acid). Of the various salts, the hydrochlorides are particularly useful, especially the hydrochlorides of Compounds No. 1, 5, 6, 14, 25, 27, 28, 29, 30, 31, 32, 33, 34, 94, 98, 103, 104, 106 and 114.

The compounds of the invention can be prepared by reacting a 2-haloquinazoline derivative of formula (II):

(in which X represents a halogen atom) with a piperazine or homopiperazine derivative of formula (III):

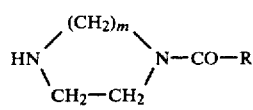

(in which m and R are as defined above).

The reaction is preferably carried out in the presence of a solvent; there is no particular limitation on the nature of the solvent employed, provided that it does not adversely affect the reaction. Preferred solvents include: aromatic hydrocarbons, such as benzene, toluene or xylene; ethers, such as diethyl ether, tetrahydrofuran or dioxan; alcohols, such as methanol, ethanol, propanol or isopentanol; esters, particularly ethyl acetate; fatty acid dimethylamides, such as dimethylformamide or dimethylacetamide; or dimethyl sulphoxide.

The temperature employed for the reaction may vary over a wide range, but is preferably from 40° to 200° C., more preferably from 60° to 150° C. The time required for the reaction will vary depending upon the reagents and the reaction temperature, but the reaction will generally be essentially complete within a period of from 1 to 24 hours.

We prefer to employ equimolar amounts of the compounds of formula (II) and (III) or a molar excess of the compound of formula (III). Preferably, the molar ratio of compound (II) to (III) is from 1:1 to 1:2.

Since the reaction is a condensation reaction proceeding via dehydrohalogenation, it can be facilitated by the presence of an acid binding agent, which may be an organic base, such as triethylamine or 1,8-diazabicyclo[5.4.0]undecene-7, or an inorganic base, such as an alkali metal hydrogen carbonate or an alkali metal carbonate.

Alternatively, the compounds of the invention can be prepared by reacting a piperazinylquinazoline or homopiperazinylquinazoline derivative of formula (IV):

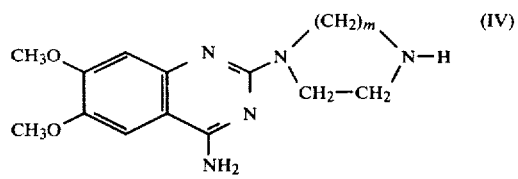

(in which m is as defined above) with a carboxylic acid of formula (V):

(in which R is as defined above) or with a reactive derivative of the carboxylic acid (V).

Suitable reactive derivatives include acid halides, acid anhydrides or mixed acid anhydrides with a monoalkylcarbonate, such reactive derivatives being well-known for the acylation of amines.

The reaction is preferably carried out in the presence of a solvent; there is no particular limitation on the nature of the solvent, provided that it does not adversely affect the reaction. Preferred solvents include: aromatic hydrocarbons, such as benzene, toluene or xylene; ethers, such as diethyl ether, tetrahydrofuran or dioxan; alcohols, such as methanol, ethanol, propanol or isopentanol; esters, particularly ethyl acetate; fatty acid dimethylamides, such as dimethylformamide or dimethylacetamide; and dimethyl sulphoxide.

The reaction may be carried out over a wide temperature range, preferably from −10° C. to +150° C., more preferably from −10° C. to +50° C. The time required for the reaction will vary, depending upon the nature of the reagents and the reaction temperature, but the reaction will generally be essentially complete within a period of from 30 minutes to 24 hours.

We prefer to employ the compounds of formulae (IV) and (V) in substantially equimolar amounts or to employ a molar excess of the compound of formula (V) or its reactive derivative. Most preferably, the molar ratio of the compound of formula (IV) to the carboxylic acid (V) or its reactive derivative is from 1:1 to 1:2.

Although the reaction between the compound of formula (IV) and the acid (V) or reactive derivative thereof will proceed without any assistance, in general it can be caused to proceed more smoothly, particularly when a reactive derivative of the acid is used, by carrying out the reaction in the presence of an acid binding agent, which may be an organic base, such as triethylamine or 1,8-diazabicyclo[5.4.0]undecene-7, or an inorganic base, such as an alkali metal hydrogen carbonate or an alkali metal carbonate.

After completion of the reaction, whichever method is used, the desired compound can be recovered by collecting, e.g. by filtration, the crystals precipitated from the reaction mixture. Alternatively, the desired compound can be obtained by concentrating the reaction mixture (e.g. by evaporation under reduced pressure), extracting the residue with an organic solvent (such as chloroform or ethyl acetate) and distilling the solvent from the extract. The product thus obtained can, if necessary, be purified by conventional means, for example by recrystallization.

Depending upon the particular process employed to prepare it, the compound of the invention may be obtained in the form of a free base or in the form of an acid addition salt; thus, for example, if the reaction employed releases free acid and if the separation and purification procedure adopted does not remove this acid, an acid addition salt will normally be obtained. Conversion of the free base to any desired salt or conversion of the salt to the corresponding free base can be conducted by conventional means either before or after the separation and purification sequence suggested above.

Biological activity

The compounds of the present invention have excellent antihypertensive activity and are thus effective for the prevention and treatment of various forms of hypertension, including essential hypertension, renal hypertension and adrenal hypertension.

The antihypertensive activity of the compounds of the invention is demonstrated by the following test.

The animals used in this test were 15 week old male spontaneously hypertensive rats. 3-5 rats were used to test each concentration of each compound. Each animal was treated as follows. The animal was anesthesized by the intraperitoneal administration of 50 mg/kg of sodium pentobarbital. A polyethylene cannula was then inserted into the abdominal aorta by the method of Weeks and Jones [J. R. Weeks and J. A. Jones, Proc. Soc. Experimental Biol. Med., 104, 646–648 (1960)]. The other end of the cannula, leading out of the body, was fixed to the neck. One week after the operation, when the animal had recovered from post-operative invasion, this end of the cannula was connected to an apparatus to measure the blood pressure and heart beat directly without the need for any further anesthesia or restraint. The haemomanometer used was an improved type of that originated by Laffan et al. [P. J. Laffan, A. Peterson, S. W. Hitch and C. Jeunelot, Cardiovascular Res., 6, 319–324 (1972)].

The compound under test was suspended at the desired concentration in a 0.3% w/v aqueous solution of carboxymethylcellulose and administered orally in a volume of 2 ml/kg body weight. The blood pressure and heart beat of each animal were observed for 1 hour before administration to give control values, and then the animal was given the sample when these values were stable. After administration of the sample, the blood pressure and heart beat of each animal were measured for 24 hours at 15 minute intervals.

For purposes of comparison, the same experiment was carried out with various concentrations of the known hypotensive agent, prazosin, in the form of its hydrochloride.

The results are shown in the following Table, in which the compounds of the invention are identified by the numbers heretofore assigned to them, and such expressions as "9 hydrochloride hydrate" mean the hydrochloride hydrate of Compound No. 9.

In the following Table, the abbreviations used are as follows:

$\Delta_{max}$ = Maximum change in blood pressure (mm/Hg) after administration of the compound under test;

$T_{max}$ = Time (in hours) after administration of the compound under test required for the blood pressure to obtain a maximum change;

$T_{0.5\ max}$ = Time (in hours) after administration of the compound under test for the blood pressure to return to one-half of its maximum value.

TABLE

| Compound | Dose (mg/kg) | $\Delta_{max}$ (mmHg) | $T_{max}$ (hour) | $T_{0.5\ max}$ (hour) |
|---|---|---|---|---|
| 1 | 3 | −35 | 0.25 | 8 |
| hydrochloride hydrate | 30 | −40 | 0.5 | 12 |
| 2 | 3 | −25 | 0.75 | 3.5 |
|  | 30 | −35 | 0.5 | 9 |
| 3 | 30 | −30 | 0.5 | 2 |
| 4 | 30 | −30 | 0.5 | 3 |
| 5 | 3 | −40 | 0.5 | 9 |
|  | 30 | −50 | 0.5 | 11.5 |
| 5 | 3 | −40 | 0.5 | 7 |
| hydrochloride | 30 | −48 | 0.75 | 14 |
| 6 | 3 | −40 | 0.5 | 8 |
|  | 30 | −65 | 0.5 | 13 |
| 7 | 3 | −20 | 0.5 | 7 |
|  | 30 | −25 | 0.5 | 15 |
| 8 | 3 | −35 | 0.5 | 4.5 |
|  | 30 | −40 | 0.5 | 7 |
| 9 | 3 | −25 | 0.5 | 3.5 |
| hydrochloride hydrate | 30 | −35 | 0.75 | 5 |
| 14 | 3 | −18 | 6 | 9.5 |
| hydrochloride dihydrate | 10 | −29 | 6–7 | 12 |
|  | 30 | −35 | 6–7 | 15 |
| 25 | 1 | −40 | 1 | 7 |
| hydrochloride hemihydrate | 3 | −70 | 1 | 14 |
| 27 | 3 | −20 | 5 | 8 |
| hydrochloride hydrate | 30 | −40 | 5 | 8 |
| 28 | 3 | −30 | 1 | 9 |
| hydrochloride hydrate | 30 | −50 | 4 | 10 |
| 29 | 3 | −30 | 2 | 8 |
| hydrochloride hydrate | 30 | −45 | 5 | 12 |
| 31 | 3 | −25 | 1–2 | 10 |
| hydrochloride hydrate | 30 | −40 | 1–2 | 14 |
| 32 | 3 | −40 | 1–2 | 10 |
| hydrochloride hydrate | 30 | −80 | 1–2 | 7 |
| 33 | 30 | −50 | 1 | 8.5 |
| hydrochloride hydrate |  |  |  |  |
| 34 | 3 | −33 | 1 | 8 |
| hydrochloride hydrate | 10 | −50 | 2 | 12 |
| 94 | 30 | −28 | 5 | 7 |
| hydrochloride hemihydrate |  |  |  |  |
| 98 | 30 | −30 | 4 | 8 |
| hydrochloride hemihydrate |  |  |  |  |

TABLE-continued

| Compound | Dose (mg/kg) | $\Delta_{max}$ (mmHg) | $T_{max}$ (hour) | $T_{0.5\ max}$ (hour) |
|---|---|---|---|---|
| 103 | 10 | −30 | 5-6 | 9.5 |
| hydrochloride sesquihydrate | 30 | −41 | 5-6 | 13 |
| prazosin hydrochloride | 3 | −35 | 0.5 | 6 |
|  | 30 | −50 | 1 | 9 |

As can be seen from the above Table, the compounds of the invention have antihypertensive activities comparable with, or in many cases significantly better than, the activity of prazosin and, with many of the compounds of the invention, the time required for the maximum effect to be realized is longer than that required by prazosin and/or the antihypertensive effect is of significantly greater duration.

Accordingly, the compounds of the invention may be used for the treatment of hypertension. The compounds may be administered orally, for example in the form of tablets, capsules, powders, microgranules, granules, solutions or suspensions. Alternatively, they may be administered parenterally, preferably in the form of an injection or suppository.

The preferred dose of the compounds of the invention will vary depending upon the type and severity of the hypertension as well as upon the activity and duration of activity of the particular compound. In general, the daily dose, when the compound is administered orally, will be within the range from 0.01 to 200 mg, but the preferred dose will vary depending upon the class of compound, as follows:

for compounds of formula (Ia) the dose is preferably from 0.1 to 200 mg per day, more preferably from 1 to 50 mg per day;

for compounds of formula (Ib), the dose is preferably from 0.1 to 200 mg per day, more preferably from 1 to 100 mg per day;

for compounds of formula (Ic) and compounds of formula (Id), the dose is preferably from 0.01 to 200 mg per day, more preferably from 0.1 to 50 mg per day; and for compounds of formula (Ie) and compounds of formula (If), the dose is preferably from 0.05 to 200 mg per day, more preferably from 0.1 to 50 mg per day.

For parenteral administration, a suitable dose is from one-third to one-tenth of the dose suggested for oral administration.

Although the compounds of the invention are quite effective by themselves for the treatment of various types of hypertension, they may also be used in conjunction with diuretics and other hypotensive agents, such as β-adrenergic receptor blocking agents.

The preparation of compounds of the invention is further illustrated by reference to the following Examples. Where necessary, certain of the piperazine starting materials may be prepared as described in "Organic Preparation and Procedures Int." 8(2) 85–86 (1976).

EXAMPLE 1

4-Amino-2-(4-crotonoyl-1-piperazinyl)-6,7-dimethoxyquinazoline hydrochloride hydrate (Compound No. 1 hydrochloride hydrate)

To 80 ml of isopentanol were added 4.55 g of 4-amino-2-chloro-6,7-dimethoxyquinazoline and 3.4 g of 1-crotonoylpiperazine; the resulting mixture was then refluxed for 1.5 hours. At the end of this time, the hot reaction mixture was filtered. The filtrate was cooled and the crystals which resulted were collected by filtration and then recrystallized from ethanol to give 3.52 g of the desired hydrochloride hydrate of Compound No. 1 in the form of colourless crystals melting at 255°–256° C. (with decomposition):

Elemental analysis: Calculated for $C_{18}H_{23}N_5O_3.HCl.H_2O$: C, 52.49%; H, 6.36%; N, 17.00%; Cl, 8.61%. Found: C, 52.88%; H, 6.24%; N, 17.17%; Cl, 8.79%.

EXAMPLE 2

4-Amino-6,7-dimethoxy-2-[4-(2-methylacryloyl)-1-piperazinyl]quinazoline (Compound No. 2)

To 20 ml of tetrahydrofuran were added 2.4 g of 4-amino-6,7-dimethoxy-2-(1-piperazinyl)quinazoline hydrochloride and 2.6 g of triethylamine, after which the mixture was stirred for 30 minutes. There was then added 0.6 g of 2-methylacryloyl chloride, after which the mixture was stirred at room temperature for 8 hours. The crystals which were produced were collected by filtration, washed with water and recrystallized from ethanol to give 0.8 g of the desired Compound No. 2 in the form of colourless needles melting at 262°–263° C. (with decomposition).

Elemental analysis: Calculated for $C_{18}H_{23}N_5O_3$: C, 60.49%; H, 6.49%; N, 19.60%. Found: C, 60.75%; H, 6.60%; N, 19.75%.

EXAMPLE 3

4-Amino-2-[4-(2,3-dimethylacryloyl)-1-piperazinyl]-6,7-dimethoxyquinazoline (Compound No. 3)

To 20 ml of tetrahydrofuran were added 2.4 g of 4-amino-6,7-dimethoxy-2-(1-piperazinyl)quinazoline hydrochloride and 2.6 g of triethylamine, after which the mixture was stirred for 20 minutes. There was then added 0.7 g of 2,3-dimethylacryloyl chloride, after which the mixture was stirred at room temperature for 12 hours. The crystals which were produced were collected by filtration, washed with water and recrystallized from ethanol, to give 1.04 g of the desired Compound No. 3 in the form of pale yellow prisms melting at 219.5°–221.5° C.

Elemental analysis: Calculated for $C_{19}H_{25}N_5O_3$: C, 61.44%; H, 6.78%; N, 18.86%. Found: C, 61.57%; H, 6.98%; N, 18.75%.

EXAMPLE 4

4-Amino-2-[4-(3,3-dimethylacryloyl)-1-piperazinyl]-6,7-dimethoxyquinazoline (Compound No. 4)

To 20 ml of tetrahydrofuran were added 2.4 g of 4-amino-6,7-dimethoxy-2-(1-piperazinyl)quinazoline hydrochloride and 2.6 g of triethylamine, after which the mixture was stirred for 20 minutes. There was then added 0.7 g of 3,3-dimethylacryloyl chloride, after which the mixture was stirred at room temperature for 15 hours. The resulting crystals were collected by filtration, washed with water and recrystallized from dimethylformamide to give 1.24 g of the desired product in the form of colourless powdery crystals melting at 278°–280° C. (with decomposition).

Elemental analysis: Calculated for $C_{19}H_{25}N_5O_3$: C, 61.44%; H, 6.78%; N, 18.86%. Found: C, 61.27%; H, 6.96%; N, 19.03%.

EXAMPLE 5

4-Amino-6,7-dimethoxy-2-[4-(2-pentenoyl)-1-piperazinyl]-quinazoline (Compound No. 5)

To 20 ml of tetrahydrofuran were added 2.4 g of 4-amino-6,7-dimethoxy-2-(1-piperazinyl)quinazoline hydrochloride and 2.6 of triethylamine, after which the mixture was stirred for 20 minutes. There was then added 0.78 g of 2-pentenoyl chloride, after which the mixture was stirred at room temperature for 15 hours. The resulting crystals were collected by filtration, washed with water and recrystallized from ethanol, to give 1.23 g of the desired Compound No. 5 in the form of pale brown needles melting at 246°–247° C.

Elemental analysis: Calculated for $C_{19}H_{25}N_5O_3$: C, 61.44%; H, 6.78%; N, 18.86%. Found: C, 61.24%; H, 6.86%; N, 18.83%.

EXAMPLE 6

4-Amino-6,7-dimethoxy-2-[4-(4-pentenoyl)-1-piperazinyl]-quinazoline (Compound No. 6)

To 20 ml of tetrahydrofuran were added 2.4 g of 4-amino-6,7-dimethoxy-2-(1-piperazinyl)quinazoline hydrochloride and 2.6 g of triethylamine, after which the mixture was stirred for 20 minutes. There was then added 0.78 g of 4-pentenoyl chloride, after which the mixture was stirred at room temperature for 15 hours. The resulting crystals were collected by filtration, washed with water and recrystallized from ethanol, to give 1.02 g of the desired Compound No. 6 in the form of pale brown needles melting at 219°–220° C.

Elemental analysis: Calculated for $C_{19}H_{25}N_5O_3$: C, 61.44%; H, 6.78%; N, 18.86%. Found: C, 61.38%; H, 6.75%; N, 18.86%.

EXAMPLE 7

4-Amino-2-[4-(3-hexenoyl)-1-piperazinyl]-6,7-dimethoxyquinazoline (Compound No. 7)

To 20 ml of tetrahydrofuran were added 2.4 g of 4-amino-6,7-dimethoxy-2-(1-piperazinyl)quinazoline hydrochloride and 2.6 g of triethylamine, after which the mixture was stirred for 20 minutes. There was then added 0.8 g of 3-hexenoyl chloride, after which the mixture was stirred at room temperature for 15 hours. The resulting crystals were collected by filtration, washed with water and recrystallized from ethanol, to give 1.10 g of the desired Compound No. 7 in the form of pale yellow powdery crystals melting at 197.5°–198.5° C.

Elemental analysis: Calculated for $C_{20}H_{27}N_5O_3$: C, 62.32%; H, 7.06%; N, 18.17%. Found: C, 62.17%; H, 7.09%; N, 18.07%.

EXAMPLE 8

4-Amino-2-[4-(2-hexenoyl)-1-piperazinyl]-6,7-dimethoxyquinazoline hemihydrate (Compound No. 8 hemihydrate)

To 15 ml of tetrahydrofuran were added 1.16 g of 4-amino-6,7-dimethoxy-2-(1-piperazinyl)quinazoline and 2.6 g of triethylamine, after which the mixture was stirred for 30 minutes. There was then added 0.53 g of 2-hexenoyl chloride, after which the mixture was stirred at room temperature for 18 hours. The reaction mixture was then concentrated by evaporation under reduced pressure and the resulting residue was washed with water and recrystallized from ethanol, to give 1.2 g of the desired Compound No. 8 hemihydrate in the form of colourless needles melting at 220°–222° C.

Elemental analysis: Calculated for $C_{20}H_{27}N_5O_3.0.5H_2O$: C, 60.89%; H, 7.15%; N, 17.75%. Found: C, 60.63%; H, 7.10%; N, 17.84%.

EXAMPLE 9

4-Amino-2-(4-crotonoyl-1-homopiperazinyl)-6,7-dimethoxyquinazoline and its hydrochloride hydrate (Compound No. 9 and its hydrochloride hydrate)

To 15 ml of tetrahydrofuran were added 1.25 g of 4-amino-2-(1-homopiperazinyl)-6,7-dimethoxyquinazoline and 2.6 g of triethylamine, after which the mixture was stirred for 30 minutes. There was then added 0.31 g of crotonoyl chloride, after which the mixture was stirred at room temperature for 15 hours. The reaction mixture was then concentrated by evaporation under reduced pressure and the resulting residue was extracted with chloroform and the extract was washed with water. The solvent was removed from the extract by distillation under reduced pressure and the residue was recrystallized from ethanol, giving 0.7 g of the desired Compound No. 9 in the form of colourless crystals melting at 200°–202° C.

Elemental analysis: Calculated for $C_{19}H_{25}N_5O_3$: C, 61.44%; H, 6.78%; N, 18.86%. Found: C, 61.32%; H, 6.91%; N, 18.78%.

The product was dissolved in ethanol and a 10% w/w solution of hydrogen chloride in ethanol was added thereto. The resulting crystals were collected by filtration, giving the desired hydrochloride hydrate, melting at 261°–263° C. (with decomposition).

Elemental analysis: Calculated for $C_{19}H_{25}N_5O_3.HCl.H_2O$: C, 53.58%; H, 6.63%; N, 16.44%; Cl, 8.32%. Found: C, 53.64%; H, 6.59%; N, 16.84%; Cl, 8.73%.

EXAMPLE 10

4-Amino-2-[4-(2,4-hexadienoyl)-1-piperazinyl]-6,7-dimethoxyquinazoline (Compound No. 10)

To 20 ml of tetrahydrofuran were added 1.16 g of 4-amino-6,7-dimethoxy-2-(1-piperazinyl)quinazoline and 1.5 g of triethylamine. There was then added 0.52 g of 2,4-hexadienoyl chloride, after which the mixture was stirred at room temperature for 3 hours. The reaction mixture was then concentrated by evaporation under reduced pressure, and the resulting residue was washed with water and recrystallized from ethanol, to give 1.3 g of the desired Compound No. 10 in the form of pale yellow powdery crystals melting at 231°–233° C.

Elemental analysis: Calculated for $C_{20}H_{25}N_5O_3$: C, 62.64%; H, 6.57%; N, 18.27%. Found: C, 62.44%; H, 6.52%; N, 18.36%.

EXAMPLE 11

4-Amino-6,7-dimethoxy-2-(4-tetroyl-1-piperazinyl)-quinazoline (Compound No. 11)

To 20 ml of ethyl acetate were added 0.32 g of sodium tetrolate (systematic name: sodium but-2-ynoate) and 0.38 g of ethyl chlorocarbonate, after which the mixture was stirred overnight. There were then added 2.6 g of triethylamine, and the mixture was stirred for 3 hours. To the resulting mixture was then added 0.4 g of 4-amino-6,7-dimethoxy-2-(1-piperazinyl)quinazoline, after which the mixture was stirred at room temperature for 15 hours. The reaction mixture was then concentrated by evaporation under reduced pressure, and the resulting residue was washed with water and recrystallized from ethanol to give 0.32 g of the desired Compound No. 11 in the form of plate yellow prisms melting at 250°-252° C.

Elemental analysis: Calculated for $C_{18}H_{21}N_5O_3$: C, 60.83%; H, 5.96%; N, 19.11%. Found: C, 60.57%; H, 6.28%; N, 19.12%.

EXAMPLE 12

4-Amino-2-[4-(2-benzyloxybenzoyl)-1-piperazinyl]-6,7-dimethoxyquinazoline hydrochloride (Compound No. 12 hydrate)

To 15 ml of isopentanol were added 0.848 g of 4-amino-2-chloro-6,7-dimethoxyquinazoline, followed by 1.05 g of 1-(2-benzyloxybenzoyl)piperazine, and the resulting mixture was heated under reflux for 2 hours. After cooling the mixture, the crystals which were produced were collected by filtration and recrystallized from methanol, to give 1.09 g of the desired Compound No. 12 hydrochloride in the form of a colourless powder melting at 215°-216° C. (with decomposition).

Elemental analysis: Calculated for $C_{28}H_{29}N_5O_4.HCl.H_2O$: C, 60.69%; H, 5.83%; N, 12.63%; Cl, 6.41%. Found: C, 60.73%; H, 5.75%; N, 12.65%; Cl, 6.42%.

EXAMPLE 13

4-Amino-2-[4-(3-benzyloxybenzoyl)-1-piperazinyl]-6,7-dimethoxyquinazoline hydrochloride hydrate (Compound No. 13 hydrochloride hydrate)

To 70 ml of isopentanol were added 3.48 g of 4-amino-2-chloro-6,7-dimethoxyquinazoline and 3.93 g of 1-(3-benzyloxybenzoyl)piperazine, and the resulting mixture was heated under reflux for 4 hours. After cooling the mixture, the crystals which were produced were collected by filtration and then recrystallized from ethanol, to give 6.59 g of the desired Compound No. 13 hydrochloride hydrate in the form of pale yellow prisms melting at 180°-182° C. (with decomposition).

Elemental analysis: Calculated for $C_{28}H_{29}N_5O_4.HCl.H_2O$: C, 60.69%; H, 5.83%; N, 12.63%; Cl, 6.40%. Found: C, 60.87%; H, 5.63%; N, 12.62%; Cl, 6.24%.

EXAMPLE 14

4-Amino-2-[4-(4-benzyloxybenzoyl)-1-piperazinyl]-6,7-dimethoxyquinazoline hydrochloride dihydrate (Compound No. 14 hydrochloride dihydrate)

To 15 ml of isopentanol were added 0.77 g of 4-amino-2-chloro-6,7-dimethoxyquinazoline and 1.04 g of 1-(4-benzyloxybenzoyl)piperazine, and the resulting mixture was heated under reflux for 2.5 hours. After cooling the mixture, the crystals which had been produced were collected by filtration and recrystallized from methanol, giving 1.63 g of the desired Compound No. 14 hydrochloride dihydrate in the form of pale yellow powdery crystals melting at 251°-253° C. (with decomposition).

Elemental analysis: Calculated for $C_{28}H_{29}N_5O_4.HCl.2H_2O$: C, 58.79%; H, 5.99%; N, 12.24%; Cl, 6.20%. Found: C, 58.41%; H, 5.61%; N, 12.14%; Cl, 6.15%.

EXAMPLE 15

4-Amino-2-[4-(4-benzyloxybenzoyl)-1-homopiperazinyl]-6,7-dimethoxyquinazoline hydrochloride dihydrate (Compound No. 15 hydrochloride dihydrate)

To 12 ml of isopentanol were added 0.72 g of 4-amino-2-chloro-6,7-dimethoxyquinazoline and 1.0 g of 1-(4-benzyloxybenzoyl)homopiperazine, and the resulting mixture was heated under reflux for 2 hours. After cooling the mixture, the crystals which had been produced were collected by filtration and recrystallized from ethanol to give 1.43 g of the desired Compound No. 15 hydrochloride dihydrate in the form of pale yellow powdery crystals melting at 167°-169° C.

Elemental analysis: Calculated for $C_{29}H_{31}N_5O_4.HCl.2H_2O$: C, 59.43%; H, 6.19%; N, 11.95%; Cl, 6.05%. Found: C, 59.43%, H, 5.94%; N, 12.05%; Cl, 5.89%.

EXAMPLE 16

4-Amino-2[4-(4-4'-chlorobenzyloxybenzoyl)-1-piperazinyl]-6,7-dimethoxyquinazoline hydrochloride (Compound No. 22 hydrochloride)

To 20 ml of isopentanol were added 0.75 g of 4-amino-2-chloro-6,7-dimethoxyquinazoline and 1.14 g of 1-[4-(4-chlorobenzyloxylbenzoyl]piperazine, and the resulting mixutre was heated under reflux for 2 hours. After cooling the mixture, the crystals which had been produced were collected by filtration and recrystallized from methanol, to give 1.35 g of the desired Compound No. 22 hydrochloride in the form of pale yellow needles melting at 269°-270° C. (with decomposition).

Elemental analysis: Calculated for $C_{28}H_{28}ClN_5O_4.HCl$: C, 58.95%; H, 5.12%; N, 12.28%; Cl, 12.43%. Found: C, 58.98%; H, 5.13%; N, 12.36%; Cl, 12.23%.

EXAMPLE 17

4-Amino-6,7-dimethoxy-2-[4-(4-4'-methylbenzyloxybenzoyl)-1-piperazinyl]quinazoline hydrochloride dihydrate (Compound No. 23 hydrochloride dihydrate)

To 15 ml of isopentanol were added 0.56 g of 4-amino-2-chloro-6,7-dimethoxyquinazoline and 0.80 g of 1-[4-(4-methylbenzyloxy)benzoyl]piperazine and the resulting mixture was heated under reflux for 4 hours. After cooling the mixture, the crystals which had been produced were collected by filtration and recrystallized from ethanol, to give 0.26 g of the desired Compound No. 23 hydrochloride dihydrate in the form of pale yellow powdery crystals melting at 235°-237° C. (with decomposition).

Elemental analysis: Calculated for $C_{29}H_{31}N_5O_4.HCl.2H_2O$: C, 60.25%; H, 6.07%; N, 11.71%; Cl, 5.93%. Found: C, 60.27%; H, 6.09%; N, 12.17%; Cl, 6.12%.

EXAMPLE 18

4-Amino-2-[4-(4-2',4'-dichlorobenzyloxybenzoyl)-1-piparazinyl]-6,7-dimethoxyquinazoline hydrochloride hemihydrate (Compound No. 24 hydrochloride hemihydrate)

To 27 ml of isopentanol were added 1.0 g of 4-amino-2-chloro-6,7-dimethoxyquinazoline and 1.68 g of 1-[4-(2,4-dichlorobenzyloxy)benzoyl]piperazine, and the resulting mixture was heated under reflux for 4 hours.

After cooling the mixture, the crystals which had been produced were collected by filtration and recrystallized from 50% v/v aqueous ethanol, to give 2.32 g of the desired Compound No. 24 hydrochloride hemihydrate in the form of pale yellow powdery crystals melting at 259°–260° C. (with decomposition).

Elemental analysis: Calculated for $C_{28}H_{27}Cl_2N_5O_4 \cdot HCl \cdot 0.5H_2O$: C, 54.78%; H, 4.76%; N, 11.41%; Cl, 17.32%. Found: C, 54.81%; H, 5.01%; N, 11.36%; N, 11.36%; Cl, 16.99%.

EXAMPLE 19

4-Amino-6,7-dimethoxy-2-[4-(4-phenethoxybenzoyl)-1-piperazinyl]quinazoline hemihydrate and its hydrochloride hydrate (Compound No. 21 hemihydrate and its hydrochloride hydrate)

To 50 ml of isopentanol were added 1.2 g of 4-amino-2-chloro-6,7-dimethoxyquinazoline and 1.7 g of 1-(4-phenethoxybenzoyl)piperazine, and the resulting mixture was heated under reflux for 3 hours. After cooling the mixture, the crystals which had been produced were collected by filtration and recrystallized from a 10% v/v solution of water in ethanol, to give 2.1 g of the desired Compound No. 21 hydrochloride hydrate in the form of colourless powdery crystals melting at 222°–224° C. (with decomposition).

Elemental analysis: Calculated for $C_{29}H_{31}N_5O_4 \cdot HCl \cdot H_2O$: C, 61.31%; H, 6.03%; N, 12.33%; Cl, 6.24%. Found: C, 61.07%; H, 6.01%; N, 12.44%; Cl, 6.16%.

This hydrochloride was then dissolved in a 10% v/v solution of water in ethanol and neutralized by the addition of a 10% w/w aqueous solution of sodium hydroxide. After concentrating the mixture by evaporation under reduced pressure, the resulting residue was recrystallized from ethanol, to give the desired Compound No. 21 hemihydrate in the form of colourless powdery crystals melting at 251°–253° C. (with decomposition).

Elemental analysis: Calculated for $C_{29}H_{31}N_5O_4 \cdot 0.5H_2O$: C, 66.65%; H, 6.17%; N, 13.40%. Found: C, 66.35%; H, 6.12%; N, 13.23%.

EXAMPLE 20

4-Amino-6,7-dimethoxy-2-[4-(2-phenoxybenzoyl)-1-piperazinyl]quinazoline hydrochloride hydrate (Compound No. 16 hydrochloride hydrate)

To 20 ml of tetrahydrofuran were added 1.16 g of 4-amino-6,7-dimethoxy-2-(1-piperazinyl)quinazoline and 1.16 g of triethylamine, and the mixture was then stirred for 30 minutes. To the resulting solution was added 0.9 g of 2-phenoxybenzoyl chloride, and the mixture was stirred at room temperature for 15 hours. The crystals which were produced were collected by filtration, washed with water and dissolved in 50% v/v ethanol-chlorform solution, after which a 10% w/w solution of hydrogen chloride in ethanol was added. The crystals produced were collected by filtration to give 1.45 g of the desired compound melting at 257°–258° C. (with decomposition) in the form of colorless powdery crystals.

Elemental analysis: Calculated for $C_{27}H_{27}N_5O_4 \cdot HCl \cdot H_2O$: C, 60.05%; H, 5.60%; N, 12.97%; Cl, 6.56%. Found: C, 59.82%; H, 5.64%; N, 12.83%; Cl, 6.39%.

EXAMPLE 21

4-Amino-6,7-dimethoxy-2-[4-(2-phenoxypropionyl)-1-piperazinyl]quinazoline hydrochloride hemihydrate (Compound No. 25 hydrochloride hemihydrate)

To 23 ml of tetrahydrofuran were added 1.16 g of 4-amino-6,7-dimethoxy-2-(1-piperazinyl)quinazoline and 1.5 g of triethylamine. There was then added 0.72 g of 2-phenoxypropionyl chloride, after which the mixture was stirred at room temperature for 15 hours. The reaction mixture was then concentrated by evaporation under reduced pressure and the residue was purified by chromatography through a silica gel column eluted with chloroform, to give 1.48 g of the desired Compound No. 25 in the form of a yellow oil. This product was dissolved in ethanol and a 10% w/w solution of hydrogen chloride in ethanol was added to the resulting solution. The crystals which were produced were collected by filtration and dried, giving 0.88 g of the desired Compound No. 25 hydrochloride hemihydrate in the form of pale yellow powdery crystals melting at 211°–213° C. (with decomposition).

Elemental analysis: Calculated for $C_{23}H_{27}N_5O_4 \cdot HCl \cdot 0.5H_2O$: C, 57.20%; H, 6.05%; N, 14.50%; Cl, 7.34%. Found: C, 57.44%; H, 6.01%; N, 14.66%; Cl, 7.40%.

EXAMPLE 22

4-Amino-6,7-dimethoxy-2-[4-(3-phenoxypropionyl)-1-piperazinyl]quinazoline hydrochloride hemihydrate (Compound No. 26 hydrochloride hemihydrate)

To 80 ml of isopentanol were added 4.55 g of 4-amino-2-chloro-6,7-dimethoxyquinazoline and 4.50 g of 1-(3-phenoxypropionyl)piperazine, and the resulting mixture was heated under reflux for 4 hours. After completion of the reaction, the hot reaction mixture was filtered and the filtrate was cooled. The crystals which were produced were collected by filtration and recrystallized from ethanol, giving 4.02 g of the desired Compound No. 26 hydrochloride hemihydrate in the form of pale yellow powdery crystals melting at 189°–191° C. (with decomposition).

Elemental analysis: Calculated for $C_{23}H_{27}N_5O_4 \cdot HCl \cdot 0.5H_2O$: C, 57.20%; H, 6.05%; N, 14.50%; Cl, 7.34%. Found: C, 57.42%; H, 6.41%; N, 14.58%; Cl, 6.95%.

EXAMPLE 23

4-Amino-6,7-dimethoxy-2-(4-phenoxyacetyl-1-piperazinyl)quinazoline hydrochloride hydrate (Compound No. 27 hydrochloride hydrate)

To 20 ml of tetrahydrofuran were added 1.16 g of 4-amino-6,7-dimethoxy-2-(1-piperazinyl)quinazoline and 1.5 g of triethylamine. There was then added to the resulting mixture 0.7 g of phenoxyacetyl chloride, and the mixture was stirred at room temperature for 4 hours. The reaction mixture was then concentrated by evaporation under reduced pressure, and the residue was extracted with chloroform. The extract was washed with water, and then the solvent was distilled from the extract under reduced pressure. The resulting residue was dissolved in ethanol, and a 10% w/w solution of hydrogen chloride in ethanol was added to this solution. The crystals thereby produced were collected by filtration and dried, to give 1.04 g of the desired Compound No. 27 hydrochloride hydrate in the form of pale yellow powdery crystals melting at 238°–240° C. (with decomposition).

Elemental analysis: Calculated for $C_{22}H_{25}N_5O_4 \cdot HCl \cdot H_2O$: C, 55.29%; H, 5.91%; N, 14.65%; Cl, 7.42%. Found: C, 55.64%; H, 5.94%; N, 14.69%; Cl, 7.50%.

EXAMPLE 24

4-Amino-6,7-dimethoxy-2-(4-phenylacetyl-1-piperazinyl)-quinazoline hydrochloride hydrate (Compound No. 28 hydrochloride hydrate)

To 20 ml of tetrahydrofuran were added 1.16 g of 4-amino-6,7-dimethoxy-2-(1-piperazinyl)quinazoline and 1.5 g of triethylamine. There was then added to the resulting mixture 0.58 g of phenylacetyl chloride, after which the mixture was stirred at room temperature for 15 hours. The reaction mixture was then concentrated by evaporation under reduced pressure and the residue was purified by chromatography through a silica gel column eluted with a 4% v/v solution of ethanol in chloroform, to give 0.5 g of an oil, which was then dissolved in ethanol. A 10% w/w solution of hydrogen chloride in ethanol was added to the resulting solution and the crystals which were thereby produced were collected by filtration and dried, to give 0.30 g of the desired Compound No. 28 hydrochloride hydrate in the form of colourless powdery crystals melting at 173°–175° C.

Elemental analysis: Calculated for $C_{22}H_{25}N_5O_3 \cdot HCl \cdot H_2O$: C, 57.20%; H, 6.11%; N, 15.16%; Cl, 7.67%. Found: C, 57.25%; H, 6.43%; N, 15.18%; Cl, 7.51%.

EXAMPLE 25

4-Amino-6,7-dimethoxy-2-[4-(3-phenylpropionyl)-1-piperazinyl]quinazoline hydrochloride hydrate (Compound No. 29 hydrochloride hydrate)

To 25 ml of tetrahydrofuran were added 1.16 g of 4-amino-6,7-dimethoxy-2-(1-piperazinyl)quinazoline and 1.5 g of triethylamine. There was then added to the resulting mixture 0.6 g of 3-phenylpropionyl chloride, after which the mixture was stirred at room temperature for 12 hours. The reaction mixture was then concentrated by evaporation under reduced pressure and the residue was extracted with chloroform. After washing the extract with water, the solvent was distilled off, and the residue was dissolved in ethanol. A 10% w/w solution of hydrogen chloride in ethanol was then added to the resulting solution and the crystals which were thereby produced were collected by filtration, giving 0.75 g of the desired Compound No. 29 hydrochloride hydrate in the form of colourless powdery crystals melting at 212°–215° C. (with decomposition).

Elemental analysis: Calculated for $C_{23}H_{27}N_5O_3 \cdot HCl \cdot H_2O$: C, 58.04%; H, 6.35%; N, 14.71%; Cl, 7.45%. Found: C, 57.60%; H, 6.31%; N, 14.69%; Cl, 7.41%.

EXAMPLE 26

4-Amino-6,7-dimethoxy-2-(4-phenylthioacetyl-1-piperazinyl)-quinazoline hydrochloride (Compound No. 30 hydrochloride)

To 25 ml of isopentanol were added 1.20 g of 4-amino-2-chloro-6,7-dimethoxyquinazoline and 1.30 g of 1-(phenylthioacetyl)piperazine, and the resulting mixture was heated under reflux for 4 hours. After cooling the mixture, the crystals which had been produced were collected by filtration and recrystallized from ethanol, giving 1.04 g of the desired Compound No. 30 hydrochloride in the form of colourless needles melting at 254°–255° C. (with decomposition).

Elemental analysis: Calculated for $C_{22}H_{25}N_5O_3S \cdot HCl$: C, 55.51%; H, 5.51%; N, 14.71%; Cl, 7.45%; S, 6.74%. Found: C, 55.43%; H, 5.50%; N, 14.58%; Cl, 7.28%; S, 6.84%.

EXAMPLE 27

4-Amino-2-(4-cyclohexylideneacetyl-1-piperazinyl)-6,7-dimethoxyquinazoline hydrochloride hydrate (Compound No. 31 hydrochloride hydrate)

To 20 ml of tetrahydrofuran were added 1.16 g of 4-amino-6,7-dimethoxy-2-(1-piperazinyl)quinazoline and 1.5 g of triethylamine, after which the mixture was stirred for 30 minutes. To this mixture was then added 0.63 g of cyclohexylideneacetyl chloride, after which the mixture was stirred at room temperature for 8 hours. The reaction mixture was then concentrated by evaporation under reduced pressure and the residue was extracted with chloroform. After washing the extract with water, the solvent was distilled off and the residue was dissolved in ethanol. A 10% w/w solution of hydrogen chloride in ethanol was then added to this solution and the crystals thereby produced were collected by filtration, giving 1.05 g of the desired Compound No. 31 hydrochloride hydrate in the form of colourless powdery crystals melting at 210°–212° C. (with decomposition).

Elemental analysis: Calculated for $C_{22}H_{28}N_5O_3 \cdot HCl \cdot H_2O$: C, 57.70%; H, 6.92%; N, 15.03%; Cl, 7.61%. Found: C, 57.79%; H, 7.18%; N, 14.71%; Cl, 7.53%.

EXAMPLE 28

4-Amino-2-(4-cyclopentylideneacetyl-1-piperazinyl)-6,7-dimethoxyquinazoline hydrochloride hydrate (Compound No. 32 hydrochloride hydrate)

To 25 ml of tetrahydrofuran were added 1.16 g of 4-amino-6,7-dimethoxy-2-(1-piperazinyl)quinazoline and 1.5 g of triethylamine, after which the mixture was stirred for 30 minutes. To this mixture was then added 0.57 g of cyclopentylideneacetyl chloride, after which the mixture was stirred at room temperature for 15 hours. The reaction mixture was then concentrated by evaporation under reduced pressure and the residue was extracted with chloroform. After washing the extract with water, the solvent was distilled off and the residue was dissolved in ethanol. A 10% w/w solution of hydrogen chloride in ethanol was then added to this solution and the crystals thereby produced were collected by filtration, giving 0.60 g of the desired Compound No. 32 hydrochloride hydrate in the form of colourless powdery crystals melting at 238°–240° C. (with decomposition).

Elemental analysis: Calculated for $C_{21}H_{26}N_5O_3 \cdot HCl \cdot H_2O$: C, 55.93%; H, 6.48%; N, 15.53%; Cl, 7.86%. Found: C, 56.23%; H, 6.84%; N, 15.65%; Cl, 7.70%.

EXAMPLE 29

4-Amino-6,7-dimethoxy-2-[4-(1-phenylcyclopropylcarbonyl)-1-piperazinyl]quinazoline hydrochloride hydrate (Compound No. 33 hydrochloride hydrate)

To 24 ml of isopentanol were added 1.2 g of 4-amino-2-chloro-6,7-dimethoxyquinazoline and 1.35 g of 1-(phenylcyclopropylcarbonyl)piperazine. The resulting mixture was heated under reflux for 4 hours and then the crystals thereby produced were collected by filtration and recrystallized from a 50% v/v aqueous ethanol, to give 1.74 g of the desired Compound No. 33 hydrochloride hydrate in the form of colourless prisms melting at 287°–288° C. (with decomposition).

Elemental analysis: Calculated for $C_{24}H_{27}N_5O_3 \cdot HCl \cdot H_2O$: C, 61.28%; H, 5.96%; N, 14.89%; Cl, 7.55%. Found: C, 61.16%; H, 6.01%; N, 14.94%; Cl, 7.70%.

EXAMPLE 30

4-Amino-6,7-dimethoxy-2-[4-(1-phenylcyclohexylcarbonyl)-1-piperazinyl]quinazoline hydrochloride hydrate (Compound No. 63 hydrochloride hydrate)

To 25 ml of isopentanol were added 1.0 g of 4-amino-2-chloro-6,7-dimethoxyquinazoline and 1.37 g of 1-(1-phenylcyclohexylcarbonyl)piperazine, and the resulting mixture was heated under reflux for 4 hours. The crystals thereby produced were collected by filtration and neutralized by the addition of a 10% w/w aqueous solution of sodium hydroxide. The resulting mixture was extracted with chloroform and the extract was subjected to silica gel chromatography and eluted with chloroform. A 10% w/w solution of hydrogen chloride in ethanol was added to the eluate and the crystals thus produced were collected by filtration, to give 0.93 g of the desired Compound No. 63 hydrochloride hydrate in the form of pale yellow powdery crystals melting at 278°–279° C. (with decomposition).

Elemental analysis: Calculated for $C_{27}H_{33}N_5O_3 \cdot HCl \cdot H_2O$: C, 63.28%; H, 6.64%; N, 13.67%; Cl, 6.93%. Found: C, 63.19%; H, 6.70%; N, 14.01%; Cl, 6.77%.

EXAMPLE 31

4-Amino-6,7-dimethoxy-2-[4-(1-phenylcyclopentylcarbonyl)-1-piperazinyl]quinazoline hydrochloride hydrate (Compound No. 60 hydrochloride hydrate)

To 25 ml of isopentanol were added 1.2 g of 4-amino-2-chloro-6,7-dimethoxyquinazoline and 1.55 g of 1-(1-phenylcyclopentylcarbonyl)piperazine, and the resulting mixture was heated under reflux for 4 hours. The crystals thus produced were collected by filtration and recrystallized from 50% v/v aqueous ethanol, to give 1.90 g of the desired compound No. 60 hydrochloride hydrate in the form of colourless powdery crystals melting at 277°–278° C. (with decomposition).

Elemental analysis: Calculated for $C_{26}H_{31}N_5O_3 \cdot HCl \cdot H_2O$: C, 60.52%; H, 6.64%; N, 13.57%; Cl, 6.87%. Found: C, 60.11%; H, 6.51%; N, 13.33%; Cl, 6.77%.

EXAMPLE 32

4-Amino-6,7-dimethoxy-2-[4-(trans-2-phenylcyclopropylcarbonyl)-1-piperazinyl]quinazoline hydrochloride dihydrate (Compound No. 34 hydrochloride dihydrate)

To 25 ml of isopentanol were added 1.2 g of 4-amino-2-chloro-6,7-dimethoxyquinazoline and 1.4 g of 1-(trans-2-phenylcyclopropylcarbonyl)piperazine, and the resulting mixture was heated under reflux for 4 hours. The crystals thus produced were collected by filtration and neutralized by the addition of a 20% w/w aqueous solution of sodium hydroxide. The resulting mixture was extracted with chloroform and the extract was charged into a silica gel chromatography column and eluted with chloroform. A 10% w/w solution of hydrogen chloride in ethanol was added to the eluate and the crystals thus produced were collected by filtration, giving 1.22 g of the desired Compound No. 34 hydrochloride dihydrate in the form of colourless powdery crystals melting at 195°–198° C. (with decomposition).

Elemental analysis: Calculated for $C_{24}H_{27}N_5O_3 \cdot HCl \cdot 2H_2O$: C, 56.97%; H, 6.37%; N, 13.84%; Cl, 7.01%. Found: C, 56.97%; H, 6.47%; N, 13.96%; Cl, 6.97%.

EXAMPLE 33

4-Amino-2-[4-(2-cyclopentyl-2-phenylacetyl)-1-piperazinyl]-6,7-dimethoxyquinazoline hydrochloride (Compound No. 79 hydrochloride)

To 25 ml of isopentanol were added 1.2 g of 4-amino-2-chloro-6,7-dimethoxyquinazoline and 1.63 g of 1-(2-cyclopentyl-2-phenylacetyl)piperazine, and the resulting mixture was heated under reflux for 4 hours. The crystals thus produced were collected by filtration and neutralized by the addition of a 10% w/w aqueous solution of sodium hydroxide. The resulting mixture was extracted with chloroform and the extract was charged into a silica gel chromatography column and eluted with chloroform. A 10% w/w solution of hydrogen chloride in ethanol was added to the eluate and the crystals thus produced were collected by filtration, giving 1.15 g of the desired Compound No. 79 hydrochloride in the form of pale yellow powdery crystals melting at 222°–224° C. (with decomposition).

Elemental analysis: Calculated for $C_{27}H_{33}N_5O_3 \cdot HCl$: C, 63.33%; H, 6.69%; N, 13.68%; Cl, 6.92%. Found: C, 63.03%; H, 6.95%; N, 13.57%; Cl, 7.02%.

EXAMPLE 34

4-Amino-2-[4-(2-cyclohexyl-2-phenylacetyl)-1-piperazinyl]-6,7-dimethoxyquinazoline hydrochloride hydrate (Compound No. 83 hydrochloride hydrate)

To 25 ml of isopentanol were added 1.2 g of 4-amino-2-chloro-6,7-dimethoxyquinazoline and 1.72 g of 1-(2-cyclohexyl-2-phenylacetyl)piperazine, and the resulting mixture was heated under reflux for 4 hours. The crystals thus produced were collected by filtration and neutralized by the addition of a 10% w/w aqueous solution of sodium hydroxide. The resulting mixture was extracted with chloroform and the extract was charged into a silica gel chromatography column and eluted with chloroform. A 10% w/w solution of hydrogen chloride in ethanol was added to the eluate and the crystals thus produced were collected by filtration, giving 1.33 g of the desired Compound No. 83 hydrochloride hydrate in the form of colourless needles melting at 224°–226° C. (with decomposition).

Elemental analysis: Calculated for $C_{28}H_{35}N_5O_3 \cdot HCl \cdot H_2O$: C, 61.81%; H, 7.04%; N, 12.87%; Cl, 6.52%. Found: C, 61.61%; H, 6.79%; N, 12.63%; Cl, 6.44%.

EXAMPLE 35

4-Amino-6,7-dimethoxy-2-[4-(4-1'-phenylethoxybenzoyl)-1-piperazinyl]quinazoline hydrochloride sesquihydrate (Compound No. 103 hydrochloride sesquihydrate)

To 20 ml of isopentanol were added 0.9 g of 4-amino-2-chloro-6,7-dimethoxyquinazoline and 1.4 g of 1-[4-(1-phenylethoxy)benzoyl]piperazine, and the resulting mixture was heated under reflux for 4 hours. The crystals thus produced were collected by filtration and neutralized by the addition of a 10% w/w aqueous solution of sodium hydroxide. The resulting mixture was then extracted with chloroform and the extract was charged into a silica gel chromatography column and eluted with a 1% v/v solution of ethanol in chloroform. A 10% w/w solution of hydrogen chloride in ethanol was then added to eluate and the resulting crystals were collected by filtration, giving 0.69 g of the desired Compound No. 103 hydrochloride sesquihydrate in the form of colourless powdery crystals melting at 181°–185° C. (with decomposition).

Elemental analysis: Calculated for $C_{29}H_{31}N_5O_4 \cdot HCl \cdot 1.5H_2O$: C, 60.33%; H, 6.11%; N, 12.14%; Cl, 6.15%. Found: C, 60.35%; H, 6.42%; N, 12.29%; Cl, 6.51%.

EXAMPLE 36

4-Amino-6,7-dimethoxy-2-[4-(4-1'-phenylethoxybenzoyl)-1-piperazinyl]quinazoline hydrochloride sesquihydrate (Compound No. 103 hydrochloride sesquihydrate)

To 20 ml of anhydrous tetrahydrofuran were added 0.9 g of 4-amino-6,7-dimethoxy-2-(1-piperazinyl)-quinazoline and 1.2 g of triethylamine. To the resulting solution was then added dropwise a solution of 0.78 g of 4-(1-phenylethoxy)benzoyl chloride in 8 ml of tetrahydrofuran, and the mixture was stirred at room temperature for 1 hour and then left to stand overnight. The reaction mixture was then concentrated by evaporation under reduced pressure and neutralized by the addition of a 10% w/w aqueous solution of sodium hydroxide. The resulting mixture was then extracted with chloroform, and the extract was charged into a silica gel chromatography column and eluted with a 1% v/v solution of ethanol in chloroform. A 10% w/w solution of hydrogen chloride in ethanol was then added to the eluate, and the resulting crystals were collected by filtration, to give 0.21 g of the desired Compound No. 103 hydrochloride sesquihydrate in the form of colourless powdery crystals having the same properties as the product of Example 35.

EXAMPLE 37

4-Amino-2-[4-(4-benzyloxy-3-methoxybenzoyl)-1-piperazinyl]-6,7-dimethoxyquinazoline hydrochloride hemihydrate (Compound No. 94 hydrochloride hemihydrate)

To 25 ml of isopentanol were added 1.2 g of 4-amino-2-chloro-6,7-dimethoxyquinazoline and 1.96 g of 1-(4-benzyloxy-3-methoxybenzoyl)piperazine, and the resulting mixture was heated under reflux for 4 hours. The resulting crystals were collected by filtration and neutralized by the addition of a 10% w/w aqueous solution of sodium hydroxide. The resulting mixture was extracted with chloroform and the extract was charged into a chromatography column and eluted with chloroform. A 10% w/w solution of hydrogen chloride in ethanol was then added to the eluate, and the resulting crystals were collected by filtration, giving 1.64 g of the desired Compound No. 94 hydrochloride hemihydrate in the form of colourless powdery crystals melting at 171°–173° C.

Elemental analysis: Calculated for $C_{29}H_{31}N_5O_5 \cdot HCl \cdot 0.5H_2O$: C, 60.57%; H, 5.78%; N, 12.18%; Cl, 6.17%. Found: C, 60.13%; H, 6.16%; N, 11.92%; Cl, 5.87%.

EXAMPLE 38

4-Amino-2-[4-(4-benzyloxy-3-chlorobenzoyl)-1-piperazinyl]-6,7-dimethoxyquinazoline hydrochloride hemihydrate (Compound No. 98 hydrochloride hemihydrate)

To 25 ml of isopentanol were added 1.27 g of 4-amino-2-chloro-6,7-dimethoxyquinazoline and 2.1 g of 1-(4-benzyloxy-3-chlorobenzoyl)piperazine, and the resulting mixture was heated under reflux for 4 hours. The resulting crystals were collected by filtration and neutralized by the addition of a 10% w/w aqueous solution of sodium hydroxide. The resulting mixture was then extracted with chloroform and the extract was charged into a silica gel chromatography column and eluted with chloroform. A 10% w/w solution of hydrogen chloride in ethanol was added to the eluate and the crystals produced were collected by filtration, to give 1.65 g of the desired Compound No. 98 hydrochloride hemihydrate in the form of colourless powdery crystals melting at 253°–254° C. (with decomposition).

Elemental analysis: Calculated for $C_{28}H_{28}N_5O_4Cl \cdot HCl \cdot 0.5H_2O$: C, 58.04%; H, 5.22%; N, 12.09%; Cl, 12.24. Found: C, 58.18%; H, 5.45%; N, 12.13%; Cl, 12.35.

EXAMPLES 39 AND 40

Following the procedures described in Example 38, the following compounds were prepared, both in the form of colourless powders:

4-amino-2-[4-(4-benzyloxy-3,5-dimethoxybenzoyl)-4-piperazinyl]-6,7-dimethoxyquinazoline hydrochloride (Compound No. 114 hydrochloride), melting at 264°–265° C. (with decomposition):

4-amino-6,7-dimethoxy-2-[4-(4-1'-phenylpropoxybenzoyl)-1-piperazinyl]quinazoline hydrochloride (Compound No. 104 hydrochloride), melting at 170°–174° C.

We claim:

1. Compounds of formula (I):

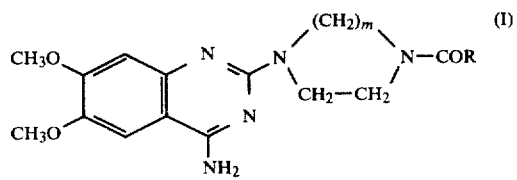

in which:

m is 2 or 3; and

R represents a group of formula:

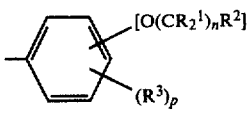

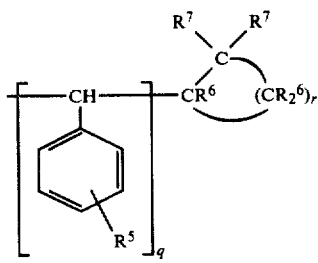

wherein
R[1] represents hydrogen or $C_1$-$C_3$ alkyl and the two R[1] groups may be the same or different;
R[2] represents phenyl or phenyl having 1 to 3 substituents selected from the group consisting of $C_1$-$C_3$ alkyl, $C_1$-$C_3$ alkoxy and halogen substituents;
R[3] represents $C_1$-$C_3$ alkyl, $C_1$-$C_3$ alkoxy, hydroxy, halogen, or a group of formula —$(O(CR^1_2)_nR^2)$ and, when there is more than one R[3], they may be the same or different;
n is 0 or an integer from 1 to 3; and
p is 0, 1 or 2;
a group of formula:

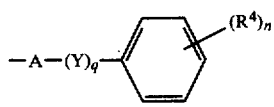

wherein
A represents $C_1$-$C_6$ straight or branched alkylene;
Y represents oxygen or sulphur;
q is 0 or 1;
R[4] represents $C_1$-$C_3$ alkyl, hydroxy group, $C_1$-$C_3$ alkoxy, halogen, amino, or amino substituted with one or two substituents selected from the group consisting of $C_1$-$C_3$ alkyl and $C_1$-$C_3$ aliphatic acyl substituents;
or a group of formula:

wherein
R[5] represents hydrogen, $C_1$-$C_3$ alkyl, $C_1$-$C_3$ alkoxy or halogen;
one of the symbols R[6] represents hydrogen, phenyl or a substituted phenyl having 1-3 substituents selected from the group consisting of $C_1$-$C_3$ alkyl, $C_1$-$C_3$ alkoxy and halogen and the other symbols R[6] all represent hydrogen atoms;
R[7] represents hydrogen, $C_1$-$C_3$ alkyl or halogen; and
r is an integer from 1 to 5;
provided that, when q is 0, one of the symbols R[6] represents said substituted or unsubstituted phenyl,
and pharmaceutically acceptable acid addition salts thereof.

2. Compounds as claimed in claim 1, having the formula (Ib):

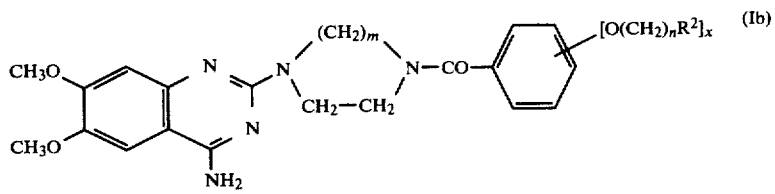

in which:
m, n and R[2] are as defined in claim 1; and
x is an integer from 1 to 3.

3. Compounds as claimed in claim 2, wherein R[2] represents phenyl or phenyl having 1 or 2 substituents selected from $C_1$-$C_3$ alkyl, $C_1$-$C_3$ alkoxy and halogen.

4. Compounds as claimed in claim 3, wherein said substituents are in the para, ortho or ortho and para positions.

5. Compounds as claimed in claim 2, wherein:
m is 2;
n is 1;
R[2] represents phenyl or phenyl having in the ortho, para or ortho and para positions one or two substituents selected from $C_1$-$C_3$ alkyl, $C_1$-$C_3$ alkoxy and halogen; and
x is 1.

6. Compounds as claimed in claim 1, having the formula (Ic):

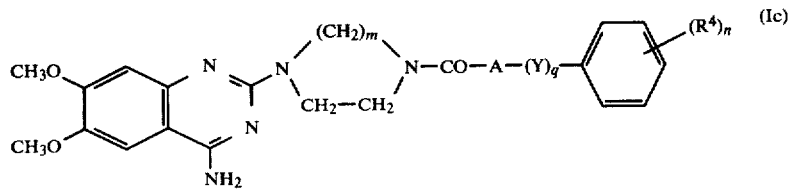

in which:

m, n, q, A, Y and $R^4$ are as defined in claim 1.

7. Compounds as claimed in claim 6, wherein $R^4$ represents $C_1-C_3$ alkyl, $C_1-C_3$ alkoxy, hydroxy or halogen.

8. Compounds as claimed in claim 6, wherein A represents a $C_1-C_6$ bivalant saturated aliphatic hydrocarbon.

9. Compounds as claimed in claim 6, wherein:

m is 2;
n is 0;
q is 0 or 1;
A represents methylene or ethylene;
Y represents an oxygen; and
$R^4$ represents substituent selected from methyl, ethyl, propyl, isopropyl, methoxy, ethoxy, propoxy and isopropoxy and fluorine, chlorine and bromine.

10. Compounds as claimed in claim 1, having the formula (Ie):

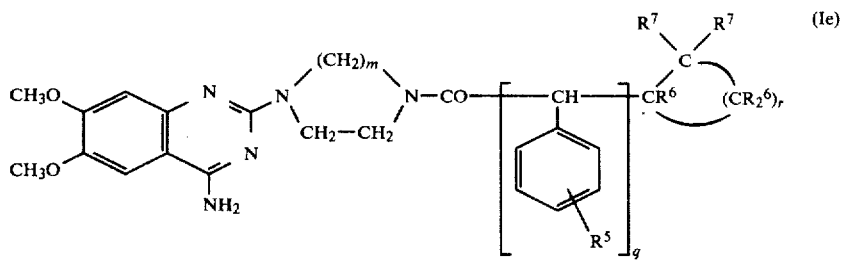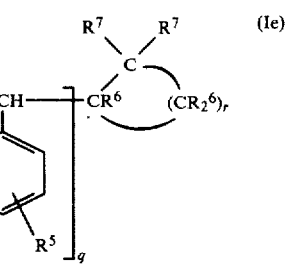

wherein $R^5$, $R^6$, $R^7$, m, q and r are as defined in claim 1.

11. Compounds as claimed in claim 10, wherein $R^5$ represents hydrogen, $C_1-C_3$ alkyl, $C_1-C_3$ alkoxy or halogen.

12. Compounds as claimed in claim 11, wherein r is 1, $R^6$ represents phenyl, the $R^7$ both represent hydrogen and m is 2.

13. Compounds as claimed in claim 1, having the formula (If):

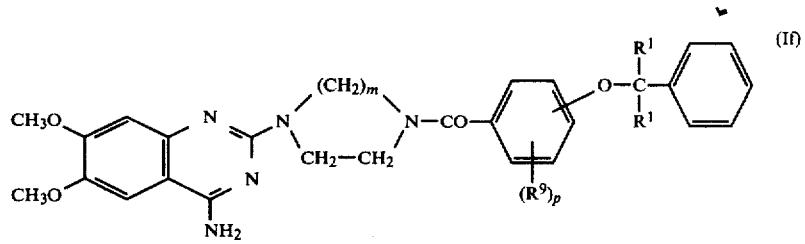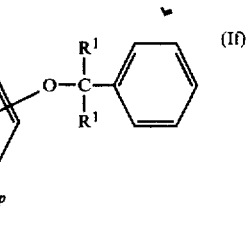

wherein:

m, p and $R^1$ are as defined in claim 1; and
$R^9$ represents alkyl, alkoxy, hydroxy or halogen.

14. Compounds as claimed in claim 13, having the formula (Ig):

15. Compounds as claimed in claim 13, where each group $R^1$ represents hydrogen or a $C_1-C_3$ alkyl.

16. Compounds as claimed in claim 14, wherein each group $R^1$ represents hydrogen or $C_1-C_3$ alkyl.

17. Compounds as claimed in claim 13, wherein one of the symbols $R^1$ represents hydrogen and the other represents hydrogen or $C_1-C_3$ alkyl.

18. Compounds as claimed in claim 14, wherein one of the symbols $R^1$ represents hydrogen and the other represents hydrogen or $C_1-C_3$ alkyl.

19. Compounds as claimed in claim 13, wherein:

m is 2;
p is 0 or 1;
one of the symbols $R^1$ represents hydrogen and the other represents hydrogen or methyl; and
$R^9$ represents $C_1-C_3$ alkyl, $C_1-C_3$ alkoxy, hydroxy, fluorine, chlorine or bromine.

20. Compounds as claimed in claim 14, wherein:

m is 2;
p is 0 or 1;
one of the symbols $R^1$ represents hydrogen and the other represents hydrogen or methyl; and
$R^9$ represents $C_1-C_3$ alkyl, $C_1-C_3$ alkoxy, hydroxy, fluorine, chlorine or bromine.

21. The compound of claim 1 which is selected from 4-amino-2-[4-(4-benzyloxybenzoyl)-1-piperazinyl]-6,7-dimethoxyquinazoline and its hydrochloride.

22. The compound of claim 1 which is selected from 4-amino-6,7-dimethoxy-2-[4-(2-phenoxypropionyl)-1-piperazinyl]quinazoline and its hydrochloride.

23. The compound of claim 1 which is selected from 4-amino-6,7-dimethoxy-2-(4-phenoxyacetyl-1-piperazinyl)quinazoline and its hydrochloride.

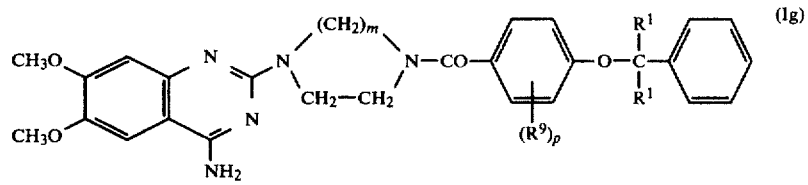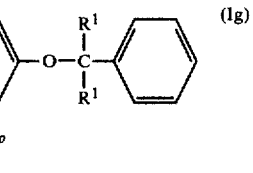

wherein m, p, $R^1$ and $R^9$ are as in claim 13.

24. The compound of claim 1 which is selected from 4-amino-6,7-dimethoxy-2-(4-phenylacetyl-1-piperazinyl)quinazoline and its hydrochloride.

25. The compound of claim 1 which is selected from 4-amino-6,7-dimethoxy-2-[4-(3-phenylpropionyl)-1-piperazinyl]quinazoline and its hydrochloride.

26. The compound of claim 1 which is selected from 4-amino-6,7-dimethoxy-2-[4-(trans-2-phehylcyclopropylcarbonyl)-1-piperazinyl]quinazoline and its hydrochloride.

27. The compound of claim 1 which is selected from 4-amino-2-[4-(4-benzyloxy-3-methoxybenzoyl)-1-piperazinyl]-6,7-dimethoxyquinazoline and its hydrochloride.

28. The compound of claim 1 which is selected from 4-amino-2-[4-(4-benzyloxy-3-chlorobenzoyl)-1-piperazinyl]-6,7-dimethoxyquinazoline and its hydrochloride.

29. The compound of claim 1 which is selected from 4-amino-6,7-dimethoxy-2-[4-(4-1'-phenylethoxybenzoyl)-1-piperazinyl]quinazoline and its hydrochloride.

30. The compound of claim 1 which is selected from 4-amino-6,7-dimethoxy-2-[4-(4-1'-phenylpropoxybenzoyl)-1-piperazinyl]quinazoline and its hydrochloride.

31. The compound of claim 1 which is selected from 4-amino-6,7-dimethoxy-2-[4-(4-α',α'-dimethylbenzyloxybenzoyl)-1-piperazinyl]quinazoline and its hydrochloride.

32. The compound of claim 1 which is selected from 4-amino-2-[4-(4-benzyloxy-3,5-dimethoxybenzoyl)-1-piperazinyl]-6,7-dimethoxyquinazoline and its hydrochloride.

33. The compounds of claim 1 which are selected from:
    4-amino-6,7-dimethoxy-2-(4-phenylthioacetyl-1-piperazinyl)quinazoline;
    4-amino-6,7-dimethoxy-2-[4-(1-phenylcyclopropylcarbonyl)-1-piperazinyl]quinazoline; and
    the hydrochlorides thereof.

34. The compound of claim 1 which is selected from 4-amino-2-[4-(4-4'-chlorobenzyloxybenzoyl)-1-piperazinyl]-6,7-dimethoxyquinazoline and its hydrochloride.

35. The compound of claim 1 which is selected from 4-amino-6,7-dimethoxy-2-[4-(4-4'-methylbenzyloxybenzoyl)-1-piperazinyl]quinazoline and its hydrochloride.

36. A pharmaceutical composition comprising, as the active ingredient, a hypotensively effective amount of a hypotensive compound in admixture with a pharmaceutically acceptable carrier or diluent, wherein said hypotensive compound is selected from the group consisting of compounds of formula (I):

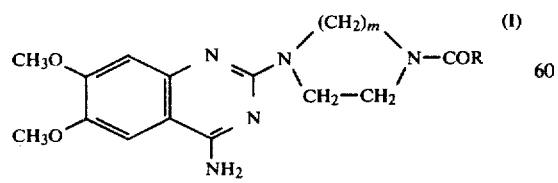

in which:
m is 2 or 3, and
R represents a group of formula:

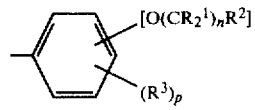

wherein
R¹ represents hydrogen, or $C_1$-$C_3$ alkyl and the two R¹ groups may be the same or different;
R² represents phenyl or phenyl having 1 to 3 substituents selected from the group consisting of $C_1$-$C_3$ alkyl, $C_1$-$C_3$ alkoxy and halogen substituents;
R³ represents $C_1$-$C_3$ alkyl, $C_1$-$C_3$ alkoxy, hydroxy, halogen or a group of formula—$(O(CR^1{}_2)_nR^2)$ and, when there is more than one R³, they may be the same or different;
n is 0 or an integer from 1 to 3; and
p is 0, 1 or 2;
a group of formula:

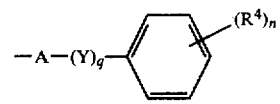

wherein
A represents $C_1$-$C_6$ straight or branched alkylene;
Y represents oxygen or sulphur;
q is 0 or 1;
R⁴ represents $C_1$-$C_3$ alkyl, hydroxy, $C_1$-$C_3$ alkoxy, halogen, amino, or an amino substituted with one or two substituents selected from the group consisting of $C_1$-$C_3$ alkyl and $C_1$-$C_3$ aliphatic acyl substituents;
or a group of formula:

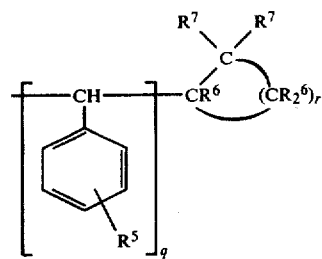

wherein
R⁵ represents hydrogen, $C_1$-$C_3$ alkyl, $C_1$-$C_3$ alkoxy or halogen;
one of the symbols R⁶ represents hydrogen, phenyl or a substituted phenyl having 1–3 substituents selected from the group consisting of $C_1$-$C_3$ alkyl, $C_1$-$C_3$ alkoxy and halogen and the other symbols R⁶ all represent hydrogen atoms;
R⁷ represents hydrogen, $C_1$-$C_3$ alkyl or halogen; and
r is an integer from 1 to 5;
provided that, when q is 0, one of the symbols R⁶ represents said substituted or unsubstituted phenyl,
and pharmaceutically acceptable acid addition salts thereof.

37. A composition as claimed in claim 36, wherein said hypotensive compound is selected from the group consisting of:
- 4-amino-2-[4-(4-benzyloxybenzoyl)-1-piperazinyl]6,7-dimethoxyquinazoline;
- 4-amino-6,7-dimethoxy-2-[4-(2-phenoxypropionyl)-1-piperazinyl]quinazoline;
- 4-amino-6,7-dimethoxy-2-(4-phenoxyacetyl-1-piperazinyl)quinazoline;
- 4-amino-6,7-dimethoxy-2-(4-phenylacetyl-1-piperazinyl)quinazoline;
- 4-amino-6,7-dimethoxy-2-[4-(-phenylpropionyl)-1-piperazinyl]quinazoline;
- 4-amino-6,7-dimethoxy-2-[4-(trans-2-phenylcyclopropylcarbonyl)-1-piperazinyl]quinazoline;
- 4-amino-2-[4-(4-benzyloxy-3-methoxybenzoyl)-1-piperazinyl]-6,7-dimethoxyquinazoline;
- 4-amino-2-[4-(4-benzyloxy-3-chlorobenzoyl)-1-piperazinyl]-6,7-dimethoxyquinazoline;
- 4-amino-6,7-dimethoxy-2-[4-(4-1'-phenylethoxybenzoyl)-1-piperazinyl]quinazoline;
- 4-amino-6,7-dimethoxy-2-[4-(4-1'-phenylpropoxybenzoyl)-1-piperazinyl]quinazoline;
- 4-amino-6,7-dimethoxy-2-[4-(4-α',α'-dimethylbenzyloxybenzoyl)-1-piperazinyl]quinazoline;
- 4-amino-2-[4-(4-benzyloxy-3,5-dimethoxybenzoyl-1-piperazinyl]-6,7-dimethoxyquinazoline;
- 4-amino-2-[4-(4-4'-chlorobenzyloxybenzoyl)-1-piperazinyl]-6,7-dimethoxyquinazoline;
- 4-amino-6,7-dimethoxy-2-[4-(4-4'-methylbenzyloxybenzoyl)-1-piperazinyl]quinazoline;

and the hydrochlorides thereof.

38. The composition of claim 36, wherein said hypotensive compound is selected from:
- 4-amino-6,7-dimethoxy-2-(4-phenylthioacetyl-1-piperazinyl)quinazoline;
- 4-amino-6,7-dimethoxy-2-[4-(1-phenylcyclopropylcarbonyl)-1-piperazinyl]quinazoline; and the hydrochlorides thereof.

39. The composition of claim 36, wherein said hypotensive compound is
4-amino-2-[4-(4-4'-chlorobenzyloxybenzoyl)-1-piperazinyl]-6,7-dimethoxyquinazoline.

40. The composition of claim 36, wherein said hypotensive compound is
4-amino-6,7-dimethoxy-2-[4-(4-4'-methylbenzyloxybenzoyl)-1-piperazinyl]quinazoline.

41. The composition of claim 36, wherein said hypotensive compound is
4-amino-2-[4-(4-benzyloxybenzoyl)-1-piperazinyl]-6,7-dimethoxyquinazoline.

42. The composition of claim 36, wherein said hypotensive compound is
4-amino-6,7-dimethoxy-2-[4-(2-phenoxypropionyl)-1-piperazinyl]quinazoline.

43. The composition of claim 36, wherein said hypotensive compound is
4-amino-6,7-dimethoxy-2-(4-phenoxyacetyl-1-piperazinyl)quinazoline.

44. The composition of claim 36, wherein said hypotensive compound is
4-amino-6,7-dimethoxy-2-(4-phenylacetyl-1-piperazinyl)quinazoline.

45. The composition of claim 36, wherein said hypotensive compound is
4-amino-6,7-dimethoxy-2-[4-(3-phenylpropionyl)-1-piperazinyl]quinazoline.

46. The composition of claim 36, wherein said hypotensive compound is
4-amino-6,7-dimethoxy-2-[4-(trans-2-phenylcyclopropylcarbonyl)-1-piperazinyl]quinazoline.

47. The composition of claim 36, wherein said hypotensive compound is
4-amino-2-[4-(4-benzyloxy-3-methoxybenzoyl)-1-piperazinyl]-6,7-dimethoxyquinazoline.

48. The composition of claim 36, wherein said hypotensive compound is
4-amino-2-[4-(4-benzyloxy-3-chlorobenzoyl)-1-piperazinyl]-6,7-dimethoxyquinazoline.

49. The composition of claim 36, wherein said hypotensive compound is
4-amino-6,7-dimethoxy-2-[4-(4-1'-phenylethoxybenzoyl)-1-piperazinyl]quinazoline.

50. The composition of claim 36, wherein said hypotensive compound is
4-amino-6,7-dimethoxy-2-[4-(4-1'-phenylpropoxybenzoyl)-1-piperazinyl]quinazoline.

* * * * *